United States Patent
Scheibel et al.

(10) Patent No.: US 10,072,152 B2
(45) Date of Patent: Sep. 11, 2018

(54) METHODS FOR PRODUCING HIGH TOUGHNESS SILK FIBRES

(71) Applicant: Amsilk GmbH, Planegg/Martinsried (DE)

(72) Inventors: Thomas Scheibel, Bayreuth (DE); Axel Leimer, Frankfurt am Main (DE); Lin Römer, Ottobrunn (DE); Lukas Eisoldt, Bayreuth (DE); Aniela Heidebrecht, Bayreuth (DE); Martha Geffers, Würzburg (DE)

(73) Assignee: AMSILK GMBH, Planegg/Martinsried (DE)

( * ) Notice: Subject to any disclaimer, the term of this patent is extended or adjusted under 35 U.S.C. 154(b) by 0 days.

(21) Appl. No.: 14/426,316

(22) PCT Filed: Sep. 5, 2013

(86) PCT No.: PCT/EP2013/068391
§ 371 (c)(1),
(2) Date: Mar. 5, 2015

(87) PCT Pub. No.: WO2014/037453
PCT Pub. Date: Mar. 13, 2014

(65) Prior Publication Data
US 2015/0284565 A1    Oct. 8, 2015

Related U.S. Application Data

(60) Provisional application No. 61/697,729, filed on Sep. 6, 2012.

(51) Int. Cl.
| | | |
|---|---|---|
| *C08L 89/00* | (2006.01) |
| *C07K 14/435* | (2006.01) |
| *B29C 47/00* | (2006.01) |
| *C08L 1/02* | (2006.01) |
| *C08L 5/02* | (2006.01) |
| *C08L 23/12* | (2006.01) |
| *C08L 33/08* | (2006.01) |
| *C08L 67/00* | (2006.01) |
| *C08L 67/04* | (2006.01) |
| *C08L 75/04* | (2006.01) |
| *C08L 77/06* | (2006.01) |
| *C08L 89/04* | (2006.01) |
| *B29L 31/00* | (2006.01) |

(52) U.S. Cl.
CPC .......... *C08L 89/00* (2013.01); *B29C 47/0004* (2013.01); *C07K 14/43518* (2013.01); *C07K 14/43586* (2013.01); *C08L 1/02* (2013.01); *C08L 5/02* (2013.01); *C08L 23/12* (2013.01); *C08L 33/08* (2013.01); *C08L 67/00* (2013.01); *C08L 67/04* (2013.01); *C08L 75/04* (2013.01); *C08L 77/06* (2013.01); *C08L 89/04* (2013.01); *B29K 2089/00* (2013.01); *B29L 2031/731* (2013.01)

(58) Field of Classification Search
None
See application file for complete search history.

(56) References Cited

U.S. PATENT DOCUMENTS

| | | | | |
|---|---|---|---|---|
| 5,994,099 A | * | 11/1999 | Lewis | C07K 14/43518 435/252.3 |
| 2004/0102614 A1 | * | 5/2004 | Islam | D01F 4/00 530/353 |
| 2007/0260039 A1 | * | 11/2007 | Karatzas | C07K 14/43518 530/324 |
| 2012/0022005 A1 | * | 1/2012 | Gat | C07K 14/43518 514/21.2 |

FOREIGN PATENT DOCUMENTS

| | | | |
|---|---|---|---|
| EP | 1609801 | * | 12/2005 |
| WO | 2006008163 A2 | | 1/2006 |
| WO | 2011069643 A2 | | 6/2011 |
| WO | 2012165476 A1 | | 12/2012 |

OTHER PUBLICATIONS

Japanese Office Action, Application No. 2015-530390, dated Sep. 21, 2017.

* cited by examiner

*Primary Examiner* — Melvin C. Mayes
*Assistant Examiner* — Colette B Nguyen
(74) *Attorney, Agent, or Firm* — MacMillan, Sobanski & Todd, LLC

(57) ABSTRACT

The present invention provides methods for producing a silk protein spinning dope solution suitable for producing high toughness fibers, the thus produced silk protein spinning dope solution, methods for producing fibers using said silk protein spinning dope solution.

7 Claims, No Drawings
Specification includes a Sequence Listing.

METHODS FOR PRODUCING HIGH TOUGHNESS SILK FIBRES

This application claims priority to PCT application No. PCT/EP2009/063891 filed Sep. 5, 2013, which claims priority to U.S. Provisional Application 61/697,729, filed Sep. 6, 2012, the disclosures of which are hereby incorporated by reference in their entirety.

The present invention provides methods for producing a silk protein spinning dope solution suitable for producing high toughness fibres, the thus produced silk protein spinning dope solution, methods for producing fibres using said silk protein spinning dope solution.

BACKGROUND OF THE INVENTION

Silk is an amazing material produced naturally by various species, such as the silk moth and silk worm (*Lepidoptera*), bees, wasps, and ants (*Hymenoptera*) and spiders (arthropods). Each species' silk has its own unique set of properties.

For example, silk from the silk moth *Bombyx mori* is ideally suited for fashion textiles due to its light weight, soft touch, and luxurious appearance. Although silks from other species, especially spider silk, have even higher toughness and tensile strength, as well as better chemical resistance—properties that make them of great interest to industry—they have not been produced commercially to date. Spiders can produce various kinds of silk—each perfectly adapted to the specific requirements demanded by nature. Orb-web-spinning spiders produce silk fibres with mechanical properties unmatched in the natural world thereby outcompeting many synthetic fibres produced by modern technology (Slotta et al. (2012) Chemical engineering process 108, 34-49).

Spider webs can withstand high deformations for example caused by the impact of prey, due to the interplay between several specialized types of silk fibres. Dragline (or major ampullate) silk forms the frame and radii of the web and serves as a lifeline for the spider during escape. Flagelliform silk, which is more-elastic, makes up the capture spiral of the net. Other silks are responsible for reproductive purposes or as glue substance, among others (Slotta et al. (2012) Chemical engineering process 108, 34-49).

Spiders are able to produce the high-performance polymer material under environmentally friendly conditions using aqueous solutions, ambient temperature, and with low energy consumption. However, the complex mechanisms behind the seemingly simple process of natural thread formation and web construction are not yet understood and therefore cannot be readily replicated.

Many attempts have been made to mimic the spinning process at the laboratory scale and significant progress has been made, but the mechanical properties of the natural dragline fibre are still unmatched.

To produce a commercial fibre, either the natural process of silk spinning must be mimicked, or a completely new spinning process must be developed. To be commercially viable, any process must be cost-efficient and environmentally friendly.

Few data on the mechanical properties of synthetic silk fibres can be found in the literature. Most of the spinning processes create fibres that are so brittle that their mechanical properties cannot be properly measured or the resulting fibres loose performance upon drying or storage.

However, these studies do provide some useful hints about the keys to spinning silk protein. For instance, a higher-molecular-weight protein produces a more-stable fibre, as reported by Xia et al. ((2010) PNAS 107: 14059-14063). Here, recombinant proteins originating from the spider *Nephila clavipes* were produced and spun into a fibre displaying mechanical properties approaching those of native silk. However, such toughness was only obtained for proteins of very high molecular weight. For recombinant spider silk proteins with a molecular weight of almost 300 kD a fibre exhibiting a toughness of 141 $MJ/m^3$ was obtained. At lower molecular weight the toughness was far inferior to native silk. These effects may be due to the reported difficulties to retain the protein at high concentrations, especially in an aqueous system.

The right combination several factors are thought to greatly improve the mechanical properties of the spun fibres. However, despite various promising approaches, the mechanical properties of natural dragline fibres have not been reproduced before.

The inventors of the present invention surprisingly found a method for producing an aqueous silk protein spinning dope solution for self-assembling polypeptides, such as spider silk polypeptides. Spinning of this dope results in fibres with a very high toughness, which tends to increase with molecular weight but is at all molecular weights superior to the toughness of silk fibres produced according to the method disclosed by Xia et. al (supra). Thus, the method of the present invention enables for the first time a unique formation of silk proteins in solution resulting in fibres with a toughness far better than reported hitherto.

SUMMARY OF THE INVENTION

In a first aspect the present invention relates to a method for producing a silk protein spinning dope solution comprising the steps:
(a) providing an aqueous solution comprising at least one silk protein and a protein denaturant or mixture of protein denaturants at a silk protein denaturing concentration, wherein the total concentration of the silk protein(s) in the solution is less than 20% w/v;
(b) reducing the concentration of the protein denaturant by 8-fold to 14-fold;
(c) reducing the concentration of the protein denaturant by 1.5 to 3-fold; and
(d) producing the silk protein spinning dope solution by concentrating the silk protein(s) in the solution at least 1.5-fold in comparison to its(their) concentration in step (a) to a concentration of at least 10% w/v.

In a second aspect the present invention relates to a method for producing a fibre comprising the steps:
(a) providing the silk spinning dope solution producible by the method of the present invention; and
(b) producing a fibre by drawing or extruding or combination thereof from the silk protein spinning dope solution.

In a third aspect the present invention relates to a spinning dope solution producible by the method of the present invention.

In a fourth aspect the present invention relates to a fibre producible by the method of the present invention.

In a fifth aspect the present invention relates to a fibre comprising at least one silk protein, wherein at least 10% by weight of the material of the fibre is(are) silk protein(s), wherein the silk protein monomer(s) has/have a molecular weight in the range of 20 kDa to 600 kDa and the fibre has a toughness ($MJ/m^3$) that is the product of the molecular weight of the silk protein(s) in kDa and the factor of at least 1.0 at least up to an molecular weight of the silk protein(s)

of 300 kDa and is at least 300 MJ/m³ for proteins with an molecular weight of above 300 kDa.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise herein, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

As used in this specification and the appended claims, the singular forms "a", "an", and "the" include plural referents, unless the content clearly dictates otherwise.

Residues in two or more polypeptides are said to "correspond" to each other if the residues occupy an analogous position in the polypeptide structures. It is well known in the art that analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (www.ebi.ac.uk/clustalw) or Align (http://www.ebi.ac.uk/emboss/align/index.html) using standard settings, preferably for Align EMBOSS: needle, Matrix: Blosum62, Gap Open 10.0, Gap Extend 0.5.

Unless otherwise indicated, the terms "polypeptide" and "protein" are used interchangeably herein and mean any peptide-linked chain of amino acids, regardless of length or post-translational modification.

The term "fibre" refers to a class of materials comprising silk proteins that are continuous filaments or are in discrete elongated pieces.

The term "toughness" refers to a property of a fibre that is measure in MJ/m³. It is well know in the art how to measure toughness of a fibre. This can be measured, for example, as described.

As mentioned above, the inventors of the present invention surprisingly found that a denatured silk protein solution, if re-natured in a controlled and unique step-wise fashion and appropriately concentrated leads to a silk protein spinning dope solution in which the proteins appear to be in a state favoring assembly of the solubilized silk proteins to form a fibre. This is attested to by the fact that the present inventors were successful in producing silk fibres of unprecedented toughness only when using the silk protein spinning dope solution produced by the method of the present invention. Accordingly, in a first aspect the present invention provides a method for producing a silk protein spinning dope solution comprising the steps:

(a) providing an aqueous solution comprising at least one silk protein and a protein denaturant or mixture of protein denaturants at a silk protein denaturing concentration, wherein the total concentration of the silk protein(s) in the solution is less than 20% w/v;

(b) reducing the concentration of the protein denaturant by 8-fold to 14-fold;

(c) reducing the concentration of the protein denaturant by 1.5 to 3-fold; and (d) producing the silk protein spinning dope solution by concentrating the silk protein(s) in the solution at least 1.5-fold in comparison to its(their) concentration in step (a) to a concentration of at least 10% w/v.

It is possible to use silk proteins as naturally occurring in the silk fibres of silkworms (e.g. *Bombyx mori*) or spiders or recombinantly produced silk proteins, which may be produced in a suitable host system comprising, for example, bacterial cells as, e.g. *E. coli*, yeast cells as, e.g. *S. pombe*, or insect cells as, e.g. Sf9 or Hi5 cells. The silk proteins used in the method of the present invention may be spider silk proteins; insect silk proteins, or mussel byssus silk proteins or variants thereof, preferably the silk proteins are spider silk proteins. It is also contemplated that mixtures of two or more silk proteins are used. Alternatively, it is possible to add other polymers and/or fibre components to the aqueous solution of step (a), (b), (c) and/or (d). Examples of such polymers include polyamide, polycaprolactone, polyacrylat, polyaramide, polylactic acid (PLA), polypropylene, polylactat, polyhydroxybutyrate, polyurethane, xanthan, cellulose, collagen, tropoelastin, elastin, keratin, cotton, wool or mixtures thereof as well as fibres made thereof.

In the embodiment, wherein another polymer is added to the silk protein(s), it is preferred that the other polymer is also soluble in the aqueous solution of step (a), (b) (c) or (d). It is more preferred that at least 20%, at least 30%, at least 40%, at least 50%, at least 60%, at least 70%, at least 80%, at least 90%, at least 95% or 100% by weight of the fibre forming material in the silk protein spinning dope solution is (are) silk proteins.

In the embodiment, wherein another polymer is added to the silk protein(s), it is preferred that the silk protein spinning dope solution comprises at least 5% by weight, at least 10% by weight, at least 15% by weight, at least 20% by weight, at least 30% by weight, at least 40% by weight, or at least 50% by weight, and/or less than 50% by weight, less than 40% by weight, less than 30% by weight, less than 20% by weight, or less than 10% by weight of the other polymer. It is, thus, particularly preferred that the content of the other polymer in the silk protein spinning dope solution is in the range of between 5% and 50% by weight, between 5% and 30% by weight, or between 5% and 20% by weight.

The spider silk protein is preferably a major ampullate silk polypeptide such as a dragline silk polypeptide, a minor ampullate silk polypeptide, or a flagelliform silk polypeptide, preferably of an orb-web spider.

Preferred orb-web spiders comprise *Araneus diadematus*, *Nephila* spp. in particular *Nephila clavipes*, *Nephila senegalensis* and *Nephila edulis*, and *Lactrodectus hesperus*. Preferred insects comprise *Lepidoptera*, particularly Bombycidae such as *Bombyx mori* or *Hymenoptera*, particularly Apoidea such as *Anthophila*.

It is preferred to use variants of such naturally occurring silk proteins, which have been optimized for their expression in heterologous hosts and for their fibre forming properties, e.g. by reducing the size and optimizing the amino acid composition. Such variants are preferably characterized by comprising naturally occurring repetitive units. It is also preferred that such silk proteins or variants thereof are self-assembling. Self-assembling proteins have the ability to form ordered macroscopic structures, e.g. fibrils or fibres. In contrast, protein aggregation generally forms amorphous unordered structures. The ability to self-assemble can be assessed, for example, by measuring of light scattering and X-Ray diffraction. The skilled person is well aware how to differentiate between a protein aggregate and the ordered structure of an assembled protein. Thus, the skilled person trying to identify a variant of a natural protein capable of self-assembly would be required to introduce one or more alterations into the protein, e.g. deletions, mutations or additions within the boundaries set out in more detail below, and investigate whether the formed structure possesses oriented and ordered properties caused by a self-assembling process as determined by light scattering and X-Ray. These measurements are preferably conducted on fibres drawn from the silk protein dope solution, which may be produced as set out in more detail below.

Preferably, the silk protein or variant thereof has a molecular weight of at least 20 kD and comprises at least two repetitive units each comprising at least one consensus sequence selected from the group consisting of:
(a) GPGXX (SEQ ID NO: 3), wherein X is any amino acid, preferably in each case independently selected from the A, S, G, Y, P, and Q;
(b) GGX, wherein X is any amino acid, preferably in each case independently selected from Y, P, R, S, A, T, N and Q; and
(c) $A_x$, wherein x is an integer from 5 to 10.

The term a "repetitive unit", as used herein, refers to a region which corresponds in amino acid sequence to a region that comprises or consists of at least one peptide motif (e.g. AAAAAA (SEQ ID NO: 13) or GPGQQ (SEQ ID NO: 4)) that repetitively occurs within a naturally occurring silk polypeptide (e.g. MaSpI, ADF-3, ADF-4, or Flag) (i.e. identical amino acid sequence) or to an amino acid sequence substantially similar thereto (i.e. variation of amino acid sequence). In this regard "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over the whole length of the respective reference naturally occurring amino acid sequence.

A "repetitive unit" having an amino acid sequence which is "substantially similar" to a corresponding amino acid sequence within a naturally occurring silk polypeptide (i.e. wild-type repetitive unit) is also similar with respect to its functional properties, e.g. a silk polypeptide comprising the "substantially similar repetitive unit" still has the ability to form a fibre. The skilled person can readily assess whether the silk polypeptide comprising a "substantially similar repetitive unit" is still capable of forming a fibre if he follows the description of how to produce a silk protein spinning dope solution and how to form a fibre using such spinning dope as set out in the experimental section.

A "repetitive unit" having an amino acid sequence which is "identical" to the amino acid sequence of a naturally occurring silk polypeptide can, for example, be a portion of a silk polypeptide corresponding to one or more peptide motifs of MaSp I (SEQ ID NO: 43) MaSp II (SEQ ID NO: 44), ADF-3 (SEQ ID NO: 1) and/or ADF-4 (SEQ ID NO: 2). A "repetitive unit" having an amino acid sequence which is "substantially similar" to the amino acid sequence of a naturally occurring silk polypeptide can, for example, be a portion of a silk polypeptide corresponding to one or more peptide motifs of MaSpI (SEQ ID NO: 43) MaSpII (SEQ ID NO: 44), ADF-3 (SEQ ID NO: 1) and/or ADF-4 (SEQ ID NO: 2), but having one or more amino acid substitution(s) at (a) specific amino acid position(s).

The term, a "repetitive unit", as used herein, does not include the non-repetitive hydrophilic amino acid domain generally thought to be present at the amino terminus and/or carboxyl terminus of naturally occurring silk polypeptides.

The term a "repetitive unit", as used herein, preferably refers to an amino acid sequence with a length of 3 to 200 amino acids, or 5 to 150 amino acids, preferably with a length of 10 to 100 amino acids, or 15 to 80 amino acids and more preferably with a length of 18 to 60, or 20 to 40 amino acids. For example, the repetitive unit according to the present invention can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 amino acids. More preferably, the repetitive unit according to the invention consists of 3, 4, 5, 6, 7, 8, 9, 10, 12, 15, 18, 20, 24, 27, 28, 30, 34, 35, or 39 amino acids. In particularly preferred embodiments, the silk protein comprises or consists of at least 50%, 60%, 65%, 70%, 75%, 80%, 85%, 90%, preferably at least 95% and most preferably 100% of multiple copies of one identical repetitive unit (e.g. $A_2$, $Q_6$, or $C_{16}$, wherein the numerical 2, 6, or 16 represent the number of repetitive units) or multiple copies of two or more different repetitive units (e.g. $(AQ)_{24}$, or $(AQ)_{12}C_{16}$). Said silk polypeptide can further be modified by adding an artificial tag to facilitate the detection or purification of said protein (e.g. T7 tag or His Tag).

The repetitive unit of the silk polypeptide can comprise or consist of an amino acid sequence of any region that comprises or consists of at least one peptide motif that repetitively occurs within a naturally occurring silk polypeptide known to one skilled in the art. Preferably, the repetitive unit of the silk polypeptide comprises or consists of an amino acid sequence of a region that comprises or consists of at least one peptide motif that repetitively occurs within an arthropod silk polypeptide, more preferably within a spider silk polypeptide, or an insect silk polypeptide. The repetitive unit of the silk polypeptide can also comprise or consist of an amino acid sequence of a region that comprises or consists of at least one peptide motif that repetitively occurs within a mussel silk polypeptide.

It is preferred that the spider silk repetitive unit comprises or consists of an amino acid sequence of a region that comprises or consists of at least one peptide motif that repetitively occurs within a naturally occurring major ampullate silk polypeptide (MaSp), such as a dragline silk polypeptide, a minor ampullate silk polypeptide (MiSp), or a flagelliform (FLAG) silk polypeptide. Most preferably, the repetitive unit comprises or consists of an amino acid sequence of a region that comprises or consists of at least one peptide motif that repetitively occurs within a naturally occurring dragline silk polypeptide or flagelliform silk polypeptide.

It is also preferred that the insect silk repetitive unit comprises or consists of an amino acid sequence of a region that comprises or consists of at least one peptide motif that repetitively occurs within a naturally occurring silk polypeptide of *Lepidoptera*. More preferably, the insect silk repetitive unit comprises or consists of an amino acid sequence of a region that comprises or consists of at least one peptide motif that repetitively occurs within a naturally occurring insect silk polypeptide of Bombycidae, most preferably of *Bombyx mori*.

The term "consensus sequence", as used herein, refers to an amino acid sequence which contains amino acids which frequently occur in a certain position (e.g. "G") and wherein, other amino acids which are not further determined are replaced by the place holder "X".

Preferably, the silk protein comprises 2 to 100 repetitive units, i.e. at least 2, 3, 4, 5, 6, 7, 8, 9, 10, 11, 12, 13, 14, 15, 16, 17, 18, 19, 20, 21, 22, 23, 24, 25, 26, 27, 28, 29, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more repetitive units. The repetitive units in the silk protein may be the same or different. It is preferred that the same repetitive unit is used in one silk protein at least 2 times, preferably 3, 4, 5, 6, 7, 8, 9, 10, 11, 12, 13, 14, 15, 16, 17, 18, 19, 20, 21, 22, 23, or 24 times. It has been observed that an increase of the length of the repetitive units increase the toughness of the resulting fibres. Accordingly, the molecular weight of the silk protein monomer is preferably between 10 kDa to 600 kDa, i.e. at least 10, 15, 20, 25, 30, 35, 40, 45, 50, 55, 60, 65, 70, 75, 80, 85, 90, 95, or 100 kDa or smaller than 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280 270, 260, 250, 240, 230, 220, 210, 200, 190, 180, 170, 160, or 150. It is, thus, particularly preferred that the molecular weight is in the range of 40 kDa to 300 kDa, more preferably 40 kDa to 200 kDa, more preferably 60 kDa to 200 kDa, more preferably 80 kDa to 180 kDa, and even more preferably of 100 kDa to 150 kDa.

In cases where the silk protein consists only of repetitive units the molecular weight of the silk protein will be as outlined above. In cases wherein the silk protein comprises further amino acid sequences, e.g. non-repetitive units and/or sequences intervening the repetitive units, e.g. linkers, the molecular weight of the silk protein will be larger. Similarly as for the molecular weight of the repetitive units within the silk protein, it has been found that the overall molecular weight of the silk protein improves the toughness of the resulting fibre. Accordingly, it is preferred that the monomer of the silk protein, comprising further amino acid sequences, preferably one or more non-repetitive units and/or sequences intervening the repetitive units, has a molecular weight between 20 kDa to 600 kDa, i.e. at least 20, 25, 30, 35, 40, 45, 50, 55, 60, 65, 70, 75, 80, 85, 90, 95, or 100 kDa or smaller than 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280 270, 260, 250, 240, 230, 220, 210, 200, 190, 180, 170, 160, or 150. It is, thus, particularly preferred that the molecular weight is in the range of 40 kDa to 300 kDa, more preferably 40 kDa to 200 kDa, more preferably 60 kDa to 200 kDa, more preferably 80 kDa to 180 kDa, and even more preferably of 100 kDa to 150 kDa.

The iterated (peptide) motifs GPGXX (SEQ ID NO: 3) and GGX, i.e. glycine rich motifs, provide flexibility to the silk polypeptide and thus, to the thread formed from the silk protein containing said motifs. In detail, the iterated GPGXX (SEQ ID NO: 3) motif forms β-turn spiral structures, which imparts elasticity to the silk polypeptide. Both major ampullate and flagelliform silks comprise a GPGXX (SEQ ID NO: 3) motif. The iterated GGX motif is associated with a helical structure having three amino acids per turn and is found in most spider silks. The GGX motif may provide additional elastic properties to the silk. The iterated polyalanine $A_x$ (peptide) motif forms a crystalline β-sheet structure that provides strength to the silk polypeptide. (WO 03/057727). The GGRPSDTYG (SEQ ID NO: 18) and GGRPSSSYG (SEQ ID NO: 19) (peptide) motifs have been selected from Resilin (WO 08/155304). Resilin is an elastomeric protein found in most arthropods (*arthropoda*). It is located in specialised regions of the cuticle, providing low stiffness and high strength (Elvin et al., Nature (473): 999-1002, 2005).

Preferred repetitive units comprise one $A_{1x}$, wherein x is an integer from 5 to 10, i.e. 5, 6, 7, 8, 9, or 10, preferably 8, and one GPGXX (SEQ ID NO: 3), wherein X is any amino acid, preferably in each case is independently selected from the A, S, G, Y, P, and Q, more preferably is Q in each instance. Another preferred repetitive unit comprises or consists of at least 2, 3, or 4, preferably at least 4 consensus sequences GPGXX (SEQ ID NO: 3), wherein X is any amino acid, preferably in each case independently selected from A, S, G, Y, P, and Q. Preferably, X is in each instance Q.

Thus, in a preferred embodiment of the present invention, the silk polypeptide comprises or consists of repetitive units each comprising at least one (e.g. 1, 2, 3, 4, 5, 6, 7, 8, or 9), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40), and GPGGS (SEQ ID NO: 11). In a further preferred embodiment of the present invention, the silk polypeptide comprises or consists of repetitive units each comprising at least one (e.g. 1, 2, 3, 4, 5, 8, 7, or 8), preferably one, amino acid sequence selected from the group consisting of GGY, GGP, GGA, GGR, GGS, GGT, GGN, and GGQ. In an additionally preferred embodiment of the present invention, the silk polypeptide comprises or consists of repetitive units each comprising at least one (e.g. 1, 2, 3, 4, 5, or 6), preferably one, amino acid sequence selected from the group consisting of AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), and AAAAAAAAAA (SEQ ID NO: 17).

In another preferred embodiment of the invention, the silk polypeptide comprises or consists of repetitive units each comprising at least one (e.g. 1, 2, 3, 4, 5, 6, 7, 8, 9, 10, 11, 12, 13, 14, 15, 16, 17, 18, 19, 20, 21, 22, 23, 24, or 25), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40), GPGGS (SEQ ID NO: 11), GGY, GGP, GGA, GGR, GGS, GGT, GGN, GGQ, AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), AAAAAAAAAA (SEQ ID NO: 17), GGRPSDTYG (SEQ ID NO: 18) and GGRPSSSYG (SEQ ID NO: 19).

Most preferably, the silk polypeptide comprises, essentially consists of, or consists of repetitive units, which comprise or consist of
i) GPGAS (SEQ ID NO: 5), AAAAAA (SEQ ID NO: 13), GGY, and GPGSG (SEQ ID NO: 6) as amino acid sequence, preferably in this order,
ii) AAAAAAAA (SEQ ID NO: 15), GPGGY (SEQ ID NO: 7), GPGGY (SEQ ID NO: 7), and GPGGP (SEQ ID NO: 8) as amino acid sequence, preferably in this order,
iii) GPGQQ (SEQ ID NO: 4), GPGQQ (SEQ ID NO: 4), GPGQQ (SEQ ID NO: 4) and GPGQQ (SEQ ID NO: 4) as amino acid sequence,
iv) GPGGA (SEQ ID NO: 9), GGP, GPGGA (SEQ ID NO: 9), GGP, GPGGA (SEQ ID NO: 9), and GGP as amino acid sequence, preferably in this order,
v) AAAAAAAA (SEQ ID NO: 15), GPGQG (SEQ ID NO: 40), and GGR as amino acid sequence, preferably in this order,
vi) AAAAAAAA (SEQ ID NO: 15), GPGGG (SEQ ID NO: 10), GGR, GGN, and GGR as amino acid sequence, preferably in this order,
vii) GGA, GGA, GGA, GGS, GGA, and GGS as amino acid sequence, preferably in this order, and/or
viii) GPGGA (SEQ ID NO: 9), GPGGY (SEQ ID NO: 7), GPGGS (SEQ ID NO: 11), GPGGY (SEQ ID NO: 7), GPGGS (SEQ ID NO: 11), and GPGGY (SEQ ID NO: 7) as amino acid sequence, preferably in this order.

Thus, in a preferred embodiment, the repetitive units of the silk polypeptide consist of module A: GPYGPGASAAAAAAGGYGPGSGQQ (SEQ ID NO: 20), module C: GSSAAAAAAAASGPGGYGPENQGPSGPGGYGPGGP (SEQ ID NO: 21), module Q: GPGQQGPGQQGPGQQGPGQQ (SEQ ID NO: 22), module S: PGSSAAAAAAAASGPGQGQGQGQGQGGRPSDTYG (SEQ ID NO: 25), module R: SAAAAAAAAGPGGGNGGRPSDTYGAPGGGNGGRPSSSYG (SEQ ID NO: 26), or variants thereof.

The silk protein may comprise combined repeats of only one of these modules or of combinations thereof. Preferred combinations are characterized as follows (the repetitive units are arranged from N- to C-terminus): XY, wherein X and Y are independently selected from A, C, Q, R and S or variant thereof and are each different, i.e. X and Y are not C at the same time. Preferred combinations that are combined with each other are CA, AC, CQ, QC, CS, SC, CR, RC, SR, RS, AQ, QA, AS, SA, AR, RA, QS, SQ, QR, RQ, SR, and RS. In further preferred combinations blocks of three repetitive units are formed, which follow the following construction scheme: XYZ, wherein X and Y are independently selected from A, C, Q, R and S or variant thereof and are each different and Z is independently selected from A, C, Q, R and S or variant thereof, is preferably identical to X. Preferred combinations that are combined with each other are CAA, CAC, CAQ, CAR, CAS, ACA, ACC. ACQ, ACR, ACS, CQA, CQC, CQQ, CQR, CQS, QCA, QCC, QCQ, QCR, QCS, CSA; CSC, CSQ, CSR, CSS, SCA, SCC, SCQ, SCR, SCS, CRA, CRC, CRQ, CRR, CRS, RCA, RCC, RCQ, RCR, RCS, SRA, SRC, SRQ, SRR, SRS, RSA, RSC, RSQ, RSR, RSS, AQA, AQC, AQQ, AQR, AQS, QAA, QAC, QAQ, QAR, QAS, ASA; ASC, ASQ, ASR, ASS, SAA, SAC, SAQ, SAR, SAS, ARA, ARC, ARQ, ARR; ARS, RAA, RAC, RAQ, RAR, RAS, QSA, QSC, QSQ, QSR, QSS, SQA, SQC, SQQ, SQR, SQS, QRA, QRC, QRQ, QRR, QRS, RQA, RQC, RQQ, RQR, RQS, SRA, SRC, SRQ, SRE, SRS, RSA, RSC, RSQ, RSR, and RSS. It is noted that it is in each case possible that one of the repetitive units is a variant of the respectively indicated repetitive unit. Accordingly, preferred repetitive units comprised in the silk proteins used in the method of the invention follow the general structure $X_m$, $XY_n$ or $XYZ_o$, wherein m is between 4 and 100, i.e. 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 or more; n is between 2 and 60, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60; and o is between 2 and 40, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40.

The terms "combined with each other" or "concatenated with each other", as used herein, mean that the modules (repetitive units) are directly combined or concatenated with each other, or mean that the modules (repetitive units) are combined or concatenated with each other via one or more spacer amino acids. Thus, in one embodiment, the modules (repetitive units) comprised in the silk polypeptide are directly combined or concatenated with each other. In another embodiment, the modules (repetitive units) comprised in the silk polypeptide are combined or concatenated with each other via one or more spacer amino acids, preferably via 1 to 25 or 1 to 20 spacer amino acids, more preferably via 1 to 15 or 1 to 10 spacer amino acids, and most preferably, via 1 to 5 spacer amino acids, e.g. via 1, 2, 3, 4, 5, 6, 7, 8, 9, 10, 11, 12, 13, 14, 15, 16, 17, 18, 19, 20, 21, 22, 23, 24, or 25 spacer amino acids. Said spacer amino acid may be any amino acid naturally occurring in proteins. Preferably, said spacer amino acid is not proline. It is preferred that the spacer amino acid contains a charged group(s). Preferably, the spacer amino acid containing a charged group(s) is independently selected from the group consisting of aspartate, glutamate, histidine, and lysine. Said spacer amino acid should be an amino acid which does not negatively affect the ability of a silk polypeptide to form a fibre. Further, said spacer amino acid should be an amino acid which does not cause steric hindrance, e.g. an amino acid having a small size such as lysine and cysteine. In more preferred embodiments, the silk polypeptide comprises modules which are directly combined with each other and modules which are combined with each other via 1 to 25 or 1 to 20 spacer amino acids, more preferably via 1 to 15 or 1 to 10 spacer amino acids, and most preferably, via 1 to 5 spacer amino acids, e.g. via 2, 3, 4, 5, 6, 7, 8, 9, 10, 11, 12, 13, 14, 15, 16, 17, 18, 19, 20, 21, 22, 23, 24, or 25 spacer amino acids.

A module A, C, Q, S, or R variant differs from the reference (wild-type) module A, C, Q, S, or R from which it is derived by up to 1, 2, 3, 4, 5, 6, 7, 8, 9, 10, 11, 12, 13, 14, or 15 amino acid changes in the amino acid sequence (i.e. substitutions, additions, insertions, deletions, N-terminal truncations and/or C-terminal truncations). Such a module variant can alternatively or additionally be characterised by a certain degree of sequence identity to the reference (wild-type) module from which it is derived. Thus, a module A, C, Q, S, or R variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference (wild-type) module A, C, Q, S, or R set out above. Preferably, the sequence identity is over a continuous stretch of at least 10, 15, 18, 20, 24, 27, 28, 30, 34, 35, or more amino acids, preferably over the whole length of the respective reference (wild-type) module A, C, Q, S, or R.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference (wild-type) module A, C, Q, S, or R. It is further particularly preferred that the sequence identity is at least 80% over a continuous stretch of at least 10, 15, 18, 20, 24, 28, or 30 amino acids, is at least 85% over a continuous stretch of at least 10, 15, 18, 20, 24, 28, or 30 amino acids, is at least 90% over a continuous stretch of at least 10, 15, 18, 20, 24, 28, or 30 amino acids, is at least 95% over a continuous stretch of at least 10, 15, 18, 20, 24, 28, or 30 amino acids, is at least 98% over a continuous stretch of at least 10, 15, 18, 20, 24, 28, or 30 amino acids, or is at least 99% over a continuous stretch of at least 10, 15, 18, 20, 24, 28, or 30 amino acids of the respective reference (wild-type) module A, C, Q, S, or R.

A fragment (or deletion variant) of module A, C, Q, S, or R has preferably a deletion of up to 1, 2, 3, 4, 5, 6, 7, 8, 9, 10, 11, 12, 13, 14, or 15 amino acids at its N-terminus and/or at its C-terminus. The deletion can also be internally.

Additionally, the module A, C, Q, S, or R variant or fragment is only regarded as a module A, C, Q, S, or R variant or fragment within the context of the present invention, if the modifications with respect to the amino acid sequence on which the variant or fragment is based do not negatively affect the ability of the silk polypeptide to self-assemble. The skilled person can readily assess whether the silk polypeptide self-assembles, for example, by measurement of light scattering and/or X-Ray diffraction.

It is more preferred that the repetitive units are independently selected from module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). The modules $A^C$ (SEQ ID NO: 29), $A^K$ (SEQ ID NO: 30), $C^C$ (SEQ ID NO: 31), $C^{K1}$ (SEQ ID NO: 32), $C^{K2}$ (SEQ ID NO: 33) and $C^{KC}$ (SEQ ID NO: 34) are variants of the module A which is based on the amino acid sequence of ADF-3 of the spider *Araneus diadematus* and of module C which is based on the amino acid sequence of ADF-4 of the spider *Araneus diadematus* (WO 2007/025719). In module $A^C$ (SEQ ID NO: 29) the amino acid S (serine) at position 21 has been replaced by the amino acid C (cysteine), in module $A^K$ (SEQ ID NO: 30) the amino acid S at position 21 has been replaced by the amino acid K (lysine), in module $C^C$ (SEQ ID NO: 31) the amino acid S at position 25 has been replaced by the amino acid 25 by C, in module $C^{K1}$ (SEQ ID NO: 32) the amino acid S at position 25 has been replaced by the amino acid K, in module $C^{K2}$ (SEQ ID NO: 33) the amino acid E (glutamate) at position 20 has been replaced by the amino acid K, and in module $C^{KC}$ (SEQ ID NO: 34) the amino acid E at position 20 has been replaced by the amino acid K and the amino acid S at position 25 has been replaced by the amino acid C (WO 2007/025719). Thus, in a more preferred embodiment, the repetitive units in the silk polypeptide consist of module $A^C$: GPYGPGASAAAAAAGGYG-PGCGQQ (SEQ ID NO: 29), module $A^K$: GPYGP-GASAAAAAAGGYGPGKGQQ (SEQ ID NO: 30), module $C^C$: GSSAAAAAAAASGPGGYGPENQGPCGPGGYG-PGGP (SEQ ID NO: 31), module $C^{K1}$: GSSAAAAAAAAS-GPGGYGPENQGPKGPGGYGPGGP (SEQ ID NO: 32), module $C^{K2}$: GSSAAAAAAAASGPGGYGPKNQGPS-GPGGYGPGGP (SEQ ID NO: 33), or module $C^{KC}$: GSSAAAAAAAASGPGGYGPKNQGPCGPGGYGPGGP (SEQ ID NO: 34).

It has been observed that the toughness of the resulting fibre can be improved, if non-repetitive units are included in the silk protein. Thus, at the same molecular weight a fibre produced from a silk protein solution comprising silk protein(s) comprising a non-repetitive unit is likely to have a higher toughness than fibres produced from a silk protein solution comprising silk proteins without a non-repetitive unit. However, if the molecular weight of the silk proteins without a non-repetitive unit is increased a similar toughness of the fibre is achieved. Thus, it is preferred that fibres comprising silk proteins without one or more non-repetitive units have a higher molecular weight. The molecular weight is preferably increased by increasing the number of repetitive units in the silk molecule. It is preferred that a silk protein without a non-repetitive unit have at least two, preferably at least three, more preferably at least four, more preferably at least five and even more preferably at least six additional repetitive units in comparison to the protein comprising at least one non-repetitive unit.

Most naturally occurring spider silk proteins also comprise at least one non-repetitive unit. Therefore, the silk protein used in the method of the present invention preferably comprises at least one non-repetitive (NR) unit. The non-repetitive unit is preferably located N-terminally, C-terminally or N-terminally and C-terminally in the silk protein. In the context of the present invention, the term "non-repetitive (NR) unit" refers to a region of amino acids present in a naturally occurring silk polypeptide that displays no obvious repetition pattern (non-repetitive unit or NR unit). NR units are protein domains with a defined tertiary structure in solution. Non-repetitive units preferably comprise charged amino acids, e.g. Glu, Asp, Lys, or Arg, which allow the formation of salt bridges between two proteins comprising a non-repetitive unit. Moreover, non-repetitive units often comprise one or more Cys residues, which allow the formation of covalent intermolecular Cys-Cys bridges between two proteins comprising a non-repetitive unit. Without wishing to be bound by any theory the inventors believe that silk protein dimers formed by Cys-Cys bridges favour the assembling of the silk proteins into fibres. Preferably, non-repetitive units comprise at least 60, at least 70, at least 80, at least 90 and more preferably at least 100 amino acids. Particularly preferred ranges are between 100 and 200 amino acids. Preferably, these repetitive units comprise at least one Cys residue.

The amino acid sequence of the non-repetitive unit corresponds to a non-repetitive amino acid sequence of naturally occurring dragline polypeptides, preferably of ADF-3 (SEQ ID NO: 1) or ADF-4 (SEQ ID NO: 2), or to an amino acid sequence substantially similar thereto. The amino acid sequence of the non-repetitive unit may also correspond to a non-repetitive amino acid sequence of black widow. More preferably, the amino acid sequence of the non-repetitive unit corresponds to a non-repetitive carboxyl-terminal amino acid sequence of naturally occurring dragline polypeptides, preferably of ADF-3 (SEQ ID NO: 1) or ADF-4 (SEQ ID NO: 2), or to an amino acid sequence substantially similar thereto. Even more preferably, the amino acid sequence of the non-repetitive unit corresponds to a non-repetitive carboxyl-terminal amino acid sequence of a silk protein, preferably a spider silk protein and even more preferably of ADF-3 (SEQ ID NO: 1) which comprises amino acids 513 through 636, or of ADF-4 (SEQ ID NO: 2) which comprises amino acids 302 through 410, or to an amino acid sequence substantially similar thereto.

On the basis of above teaching and by sequence comparison the skilled person is capable of identifying further non-repetitive units in silk an in particular in spider silk proteins that are suitable to be used in the context of the method of the present invention.

In this regard "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over 20, 30, 40, 50, 60, 70, 80 or more amino acids, more preferably over the whole length of the respective reference non-repetitive (carboxyl terminal) amino acid sequence of naturally occurring dragline polypeptides, preferably of ADF-3 (SEQ ID NO: 1) or ADF-4 (SEQ ID NO: 2). A "non-repetitive unit" having an amino acid sequence which is "substantially similar" to a corresponding non-repetitive (carboxyl terminal) amino acid sequence within a naturally occurring dragline polypeptide (i.e. wild-type non-repetitive (carboxyl terminal) unit), preferably within ADF-3 (SEQ ID NO: 1) or ADF-4 (SEQ ID NO: 2), is also similar with respect to its functional properties, e.g. a silk polypeptide comprising the "substantially similar non-repetitive unit" still has the ability to self-assemble. The skilled person can readily assess whether the silk polypeptide comprising the "substantially similar non-repetitive unit" self-assembles, for example, by measurement of light scattering and/or X-Ray diffraction.

Most preferably, the non-repetitive (NR) unit is NR3 (SEQ ID NO: 41); NR4 (SEQ ID NO: 42); NR5 (SEQ ID NO: 45); or NR6 (SEQ ID NO: 46); or variants thereof. A NR3, NR4, NR5, or NR6 non-repetitive unit variant differs from the reference NR3 (SEQ ID NO: 41), NR4 (SEQ ID NO: 42), NR5 (SEQ ID NO: 45); or NR6 (SEQ ID NO: 46) non-repetitive unit from which it is derived by up to 1, 2, 3, 4, 5, 6, 7, 8, 9, 10, 11, 12, 13, 14, 15, 16, 17, 18, 19, 20, 25, or 30 amino acid changes in the amino acid sequence (i.e. exchanges, insertions, deletions, N-terminal truncations and/or C-terminal truncations). Such a NR3, NR4, NR5, or NR6 unit variant can alternatively or additionally be characterised by a certain degree of sequence identity to the reference NR3, NR4, NR5, or NR6 non-repetitive unit from which it is derived. Thus, a NR3, NR4, NR5, or NR6 non-repetitive unit variant has a sequence identity of at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference NR3, NR4, NR5, or NR6 non-repetitive unit. Preferably, the sequence identity is over a continuous stretch of at least 10, 20, 30, 40, 50, 60, 70, 80, 90, or more amino acids, preferably over the whole length of the respective reference NR3, NR4, NR5, or NR6 non-repetitive unit.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference NR3, NR4, NR5, or NR6 non-repetitive unit. It is further particularly preferred that the sequence identity is at least 80% over a continuous stretch of at least 20, 30, 40, 50, 60, 70, or 80 amino acids, is at least 85% over a continuous stretch of at least 20, 30, 40, 50, 60, 70, or 80 amino acids, is at least 90% over a continuous stretch of at least 20, 30, 40, 50, 60, 70, or 80 amino acids, is at least 95% over a continuous stretch of at least 20, 30, 40, 50, 60, 70, or 80 amino acids, is at least 98% over a continuous stretch of at least 20, 30, 40, 50, 60, 70, or 80 amino acids, or is at least 99% over a continuous stretch of at least 20, 30, 40, 50, 60, 70, or 80 amino acids of the respective reference NR3, NR4, NR5, or NR6 non-repetitive unit.

A fragment (or deletion variant) of a NR3, NR4, NR5, or NR6 non-repetitive unit has preferably a deletion of up to 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, or 60 amino acids at its N-terminus and/or at its C-terminus. The deletion can also be internally.

Additionally, the NR3, NR4, NR5, or NR6 non-repetitive unit variant or fragment is only regarded as a NR3, NR4, NR5, or NR6 non-repetitive unit variant or fragment within the context of the present invention, if the modifications with respect to the amino acid sequence on which the variant or fragment is based do not negatively affect the ability of a silk polypeptide to self-assemble. The skilled person can readily assess whether the silk polypeptide comprising a NR3, NR4, NR5, or NR6 non-repetitive unit variant or fragment self-assembles, for example, by measurement of light scattering and/or X-Ray diffraction.

It is particularly preferred that the silk protein used in the method of the invention is selected from the group consisting of ADF-3 (SEQ ID NO: 1), ADF-4 (SEQ ID NO: 2), MaSp I (SEQ ID NO: 43), or MaSp II (SEQ ID NO: 44); or variants thereof; or $(C)_m$, $(C)_m NR_z$, $NR_z(C)_m$, $NR_z(C)_m NR_z$, $(AQ)_n$, $(AQ)_n NR_z$, $NR_z(AQ)_n$, $NR_z(AQ)_n NR_z$, $(QAQ)_o$, $NR_z(QAQ)_o$, $(QAQ)_o NR_z$, wherein m is an integer of 4 to 64, i.e. 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64; n is an integer of 10 to 40, i.e. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, o is an integer of 8 to 40, i.e. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40; and z is an integer of 1 to 3, i.e. 1, 2 or 3; and NR is in each case independently a non-repetitive unit, preferably NR3, NR4, NR5, or NR6 non-repetitive unit or variant thereof.

The above mentioned formulas are defined by one of the following: In the formula i) $(C)_m$, a "m" number of C modules, namely 8 to 64 C modules, represented by the amino acid sequence according to SEQ ID NO: 21, are combined with each other ii) $(C)_m NR_z$, a "m" number of C modules, namely 8 to 48 C modules, represented by the amino acid sequence according to SEQ ID NO: 21, are combined with each other, wherein said C modules are further combined with a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 45, or NR6 represented by the amino acid sequence according to SEQ ID NO: 46, iii) $NR_z(C)_m$, a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 45, or NR6 represented by the amino acid sequence according to SEQ ID NO: 46, is present (z=1) or are combined with each other (z =2 or 3), wherein said non-repetitive (NR) unit(s) is (are) further combined with a "m" number of C modules, namely 2 to 64 C modules, represented by the amino acid sequence according to SEQ ID NO: 21, iv) $(AQ)_n$, a "n" number of A and Q module combinations, namely 6 to 36 A and Q module combinations, wherein module A is represented by the amino acid sequence according to SEQ ID NO: 20 and module Q is represented by the amino acid sequence according to SEQ ID NO: 22, are combined with each other, v) $(AQ)_n NR_z$, a "n" number of A and Q module combinations, namely 10 to 40 A and Q module combinations, wherein module A is represented by the amino acid sequence according to SEQ ID NO: 20 and module Q is represented by the amino acid sequence according to SEQ ID NO: 22, are combined with each other, and wherein said A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 45, or NR6 represented by the amino acid sequence according to SEQ ID NO: 46, vi) $NR_z(AQ)_n$, a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 45, or NR6 represented by the amino acid sequence according to SEQ ID NO: 46, is present (z=1) or are combined with each other (z=2 or 3), wherein said non-repetitive (NR) unit(s) is (are) further combined with a "n" number of A and Q module combinations, namely 10 to 40 A and Q module combinations, wherein module A is represented by the amino acid sequence according to SEQ ID NO: 20 and module Q is represented by the amino acid sequence according to SEQ ID NO: 22, vii) $(QAQ)_o$, a "o" number of Q, A and Q module combinations, namely 8 to 24 Q, A and Q module combinations, wherein module Q is represented by an amino acid sequence according to SEQ ID NO: 22 and module A is represented by the amino acid sequence according to SEQ ID NO: 20, are combined with each other, viii) $(QAQ)_o NR_z$, a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, are combined with each other, and wherein said Q, A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 45, or NR6 represented by the amino acid sequence according to SEQ ID NO: 46, and ix) $NR_z(QAQ)_o$, a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 45, or NR6 represented by the amino acid sequence according to SEQ ID NO: 46, is present (z=1) or are combined with each other (z=2 or 3), wherein said non-repetitive (NR) unit(s) is (are) further combined with a "o" number of Q, A and Q module combinations, namely 8 to 40 Q, A and Q module combinations, wherein module Q is represented by an amino acid sequence according to SEQ ID NO: 22 and module A is represented by the amino acid sequence according to SEQ ID NO: 20.

In the most preferred embodiments the silk protein that is used in the method of the present invention is $C_8NR4$, $C_{16}NR4$, $C_{32}NR4$, $(AQ)_{12}NR3$, $(AQ)_{24}NR3$, $(AQ)_{24}$, $C_{32}$, $NR4C_{16}NR4$, $NR4C_{32}NR4$, $NR3C_{16}NR3$, $NR3C_{32}NR3$, $NR4(AQ)_{12}NR4$, $NR4(AQ)_{24}NR4$, $NR3(AQ)_{12}NR3$, $NR3(AQ)_{24}NR3$, $(QAQ)_{16}$, $NR5C_{16}NR4$, $NR6C_{16}NR4$, $NR5C_{32}NR4$, $NR6C_{32}NR4$, $NR5C_{16}NR3$, $NR6C_{16}NR3$, $NR5C_2NR3$, $NR6C_{16}NR3$, $NR5(AQ)_{12}NR4$, $NR6(AQ)_{12}NR4$, $NR5(AQ)_{24}NR4$, $NR6(AQ)_{24}NR4$, $NR5(AQ)_{12}NR3$, $NR6(AQ)_{12}NR3$, $NR5(AQ)_{24}NR3$, or $NR6(AQ)_{24}NR3$.

The denaturing agent serves the purpose of substantially unfolding the silk proteins, i.e. to destroy the quaternary, tertiary and preferably also secondary structure of the silk protein. This allows inter alia the solubilisation of insoluble recombinantly expressed silk protein and the subsequent controlled transition of the denatured proteins into a state, which is suitable to form fibres of high toughness. The phrase that the denaturing agent is comprised in the solution in a "silk protein denaturing concentration" has to be understood to refer to a concentration of the denaturing agent, in which the silk protein has substantially lost or lost its tertiary and preferably also its secondary structure. Preferably, the protein is present in a so called random coil structure. The skilled person is well aware of various methods of how to measure whether a given silk protein is denatured in the solution in above outlined sense. These methods include inter alia protein nuclear magnetic resonance spectroscopy (protein NMR) and circular dichroism (CD). The "silk protein denaturing concentration" for a given denaturing agent will also depend on the pH, the temperature and the presence of other salts, e.g. buffers. The respectively required concentration of a denaturing agent can be determined without undue burden for a given solution. The concentration of a given denaturant required to denature the silk protein to the extent required in the context of the method of the invention will also depend on the further conditions in the aqueous solution of step (a). Preferably, the temperature of the aqueous solution is between 4° C. and 30° C., more preferably between 15° C. and 25° C. and/or the pH is between pH 5 and 9, preferably between 6 and 8, It is also preferred that salts are present in a concentration of between 0.01 to 1 M, preferably of between 0.1 and 0.5 M. Thus, the concentration of the respective denaturing agent is preferably selected to denature the silk protein under above indicated preferred conditions.

It has been observed by the present inventors that guanidinium salts are particularly suitable as denaturing agents in the context of step (a) of the method of the present invention. The most preferred denaturant for denaturing the silk protein in step (a) is guanidinium thiocyanate.

For guanidinium salts preferred protein denaturing concentrations are in the range of 5 M to 8 M. These concentrations are preferably employed when the aqueous solution provided in step (a) has a temperature of between 4° C. and 30° C., more preferably between 15° C. and 25° C. and/or the pH is between pH 5 and 9, preferably between pH 6 and pH 8 and/or salts are present in a concentration of between 0.01 to 1 M.

It is preferred that the aqueous solution provided in step (a) comprises a buffer to adapt the pH. Suitable buffers include Tris-HCl, Hepes, MOPS, phosphate-buffer, $NaHCO_3/Na_2CO_3$. The buffers are provided in concentrations typical for protein solutions. Preferred salts that may be comprised in the aqueous solution provided in step (a) comprise NaCl, and/or KCl Preferred concentrations of such salts are between 0.1 to 0.5 M.

The concentration of the silk protein in the aqueous solution provided in step (a) is chosen such that it is below the desired concentration in the silk protein spinning dope solution, which is the result of step (d). Preferably, it is in the range of 4 to 15% w/v, i.e. 4, 5, 6, 7, 8, 9, 10, 11, 12, 13, 14 or 15, more preferably in the range of 6 to 12% w/v.

The present inventors have determined that it is advantageous for obtaining the state of the silk protein that allows the formation of fibres with high toughness, if the guanidinium salt concentration, which may be comprised in aqueous solution provided in step (a) is reduced prior to step (d), e.g. in an additional dialysis step after step (c) but prior to step (d) or during step (d) at least 100-fold, preferably at least 200-fold.

The purpose of step (d) is the increase of the concentration of the spider silk to a concentration that is suitable for producing fibres. Such concentration is preferably at least 10% w/v, more preferably at least 12% w/v, more preferably at least 15% w/v, more preferably at least 20% w/v, more preferably at least 25% w/v. The removal of the denaturing agent in steps (b) and (c) may be continued in step (d).

It is preferred that a chemical chaperone is present in the aqueous silk protein solution in step (a), (b), and/or (c) or the spinning dope solution produced in step (d). The term "chemical chaperone" refers in the context of the present invention to molecules which aid protein folding and/or increase protein solubility. The chemical chaperone sodium phenylbutyrate, for example, appears to act by masking of hydrophobic domains that have formed in the proteins during folding. Through these effects chemical chaperones counteract the tendency of proteins in solution to aggregate (see e.g. Bathaie, B. B. et al. (2011) The Protein J. 30 (7), 480-489). Preferred chemical chaperones that may be used in the context of the method of the present invention comprise dimethylsulfoxide (DMSO), polyamine, like e.g. spermine or spermidine, polyole, like glycerine, urea, mono or disaccharides, e.g. trehalose, cholic acid, sodium phenylbutyrate or trimethylamine N-oxide. For the purpose of this invention, urea in a concentration up to 1 M is defined as a chemical chaperone. Urea is a particularly preferred chemical chaperone, which acts as a chemical chaperon at concentration of less than 1 M. Preferably, the aqueous silk protein solutions in step (a), (b) and/or (c) or the silk protein spinning dope solution of step (d) comprise the chemical chaperone at a concentration of less than 1 M, preferably between 0.25 and 0.75 M. The presence of a chemical chaperone appears to stabilize the state of the silk protein that is capable of forming fibres of high toughness, thus, it is particularly preferred that the chemical chaperone is present in step (d) and in the resulting silk protein spinning dope solution.

It is preferred that steps (b), (c) and (d) are carried out subsequently in this order. However, depending on the method used to reduce the concentration of the protein denaturant in steps (b) and (c) the silk protein concentration may be increased at the same time. While it is preferred that the concentration is not significantly increased in steps (b) and (c), in one embodiment the concentration is increased at the same time when reducing the denaturant concentration. Thus, in one embodiment steps (b) and (d) and/or steps (c) and (d) are carried out concomitantly.

The reducing of the concentration of the protein denaturant in steps (b) and/or (c) can be carried out by any art known method. Preferably it is carried out by dialysis and/or diafiltration.

Dialysis is typically carried out using a dialysis membrane with a defined molecular weight cut of that retains the silk protein on one side of the dialysis membrane and separates it from the dialysis solution on the other side of the membrane. Typically an excess of dialysis solution is provided. It is preferred that this solution comprises the components, e.g. denaturants, at the concentration desired as endpoint of the respective dialysis step, e.g. if the denaturant concentration is reduced 8-fold to 14-fold the concentration of the denaturant in the dialysis solution is 8-fold to 14-fold lower than the concentration in the aqueous solution provided in step (a). Accordingly, dialysis allows changing the composition of the aqueous solution comprising the silk protein by providing a dialysis buffer of the desired composition, e.g. the pH may be altered or the salt concentration may be increased, while reducing the concentration of the denaturant. Typically, there is also a small change in the volume of the dialysed aqueous silk protein solution, which may lead to an increase in the concentration of the silk protein in the aqueous solution. This change may be compensated for by the addition of aqueous solution. It is preferred that aqueous solution is added with a composition similar or identical to the dialysis solution. It is also possible to add aqueous solution, which is similar or identical to the dialysis solution but for the concentration of the denaturant. The later approach may allow a more rapid decrease of the concentration of the denaturant, preferably of the guanidinium salt.

In another preferred embodiment the concentration of the denaturant is reduced by diafiltration, preferably by tangential flow filtration (TFF). In TFF, typically, the silk protein comprising solution flows parallel to the filter membrane. A pressure differential across the membrane causes fluid and filterable solutes (whose molecular weight is smaller than that of the membranes or behaves in this way, such as globular proteins) to flow through the filter. Diafiltration can be either discontinuous or continuous diafiltration, e.g. TFF. In discontinuous diafiltration, the solution is concentrated, and the lost volume is replaced by a new aqueous solution. Preferably, the lost volume is continuously replaced by new aqueous solution to minimize or prevent concentration of the silk proteins in the aqueous solution. In continuous diafiltration, the solution volume is maintained by the inflow of new buffer solution while the old buffer solution is removed. In both cases it is preferred that the aqueous solution comprises the denaturant to be removed, preferably the guanidinium salt in the desired end concentration of the respective step, i.e. step (b), step (c) and/or step (d).

The reduction of the concentration of the denaturant in step (b) is preferably by 8-fold, 9-fold, 10-fold, 11-fold, 12-fold, 13-fold or 14-fold. Thus, if the concentration of the denaturant in the aqueous solution provided in step (a) is 7 M than it is preferred that the concentration at the completion of step (b) is between 0.875 M and 0.5 M.

During removal of the denaturant the silk protein partially enters an equilibrium state reflecting the respective denaturant concentration in the aqueous solution. This a process that requires some time and it is, therefore, preferred that step (b) is carried out for at least 30 min, more preferably for at least 1 h, more preferably for at least 2 h, more preferably for at least 4 h, more preferably for at least 6 h, more preferably for at least 8 h, more preferably for at least 10 h. For dialysis the equilibrium state may be achieved by allowing the aqueous silk protein sample to contact the dialysis solution for the indicated period of time. For diafiltration the equilibrium state may be achieved by choosing the conditions of diafiltration in such that the respective reduction of the denaturant concentration is gradually achieved over the indicated time periods or preferred time periods.

In a preferred embodiment the concentration of the denaturant is between 0.6 M to 0.4 M at the end of step (b). In particular if the denaturant used in step (a) is a guanidinium salt the guanidinium salt concentration is reduced to between 0.6 M to 0.4 M, preferably to 0.5 M at the end of step (b).

It is preferred that step (b) is carried out at a temperature between 4° C. and 30° C., preferably between 15° C. and 25° C.

It is preferred that the concentration of the components of the aqueous solution with the exception of the denaturant are not altered during step (b), although the silk protein concentration may vary slightly depending on the composition of the dialysis buffer or the conditions of the diafiltration.

The reduction of the concentration of the denaturant in step (c) is preferably by 1.5-fold, 1.6-fold, 1.7,-fold, 1.8-fold, 1.9-fold, 2.0-fold, 2.1-fold, 2.2.-fold, 2.3-fold, 2.4-fold, 2.5-fold, 2.6-fold, 2.7-fold, 2.8-fold, 2.9-fold or 3-fold. To provide the silk protein with sufficient time to enter the equilibrium state it is preferred that step (c) is carried out for at least 30 min, more preferably for at least 1 h, more preferably for at least 2 h, more preferably for at least 4 h, more preferably for at least 6 h, more preferably for at least 8 h, more preferably for at least 10 h.

It is preferred that step (c) is carried out at a temperature between 4° C. and 30° C., preferably between 15° C. and 25° C.

In particular if the denaturant used in step (a) is a guanidinium salt the guanidinium salt concentration is reduced to between 0.3 M to 0.2 M, preferably to about 0.25 M at the end of step (c).

The concentrating in step (d) can be achieved by any method known in the art for increasing the concentration of a protein in aqueous solution. In a particularly useful embodiment, the silk protein is concentrated by dialysis or by filtration. Dialysing is preferably carried out against a dehydrating solution such as a solution comprising a hygroscopic polymer. Examples of suitable hygroscopic polymers include, but are not limited to, polyethylene glycol (PEG), amylase, and sericin, or a combination of two or more thereof. PEG molecules are available in a range of molecular sizes and the selection of the PEG will be determined by the membrane chosen for dialysis and the rate of concentration required. Preferably, the PEG is of a molecular weight of about 8,000 to about 10,000 g/mol and has a concentration of about 25% to about 50%. In some embodiments, the separation can be conducted by membrane-filtration, which includes, but is not limited to, methods such as single pass, dead-end, direct flow filtration (DFF), and cross-flow or tangential flow filtration (TFF). Filtration is based on the principle of separating molecules according to size using a semi-permeable membrane of a defined range of pore sizes. It is known to those skilled in the art that combinations of filtration methods and membrane types may be used in separation. According to the invention, membrane-filtration is the separation of cellular components effected by polymeric or inorganic membranes. Within the art, there are four commonly accepted categories of membranes defined by the size of the material they remove from the carrier liquid. Methods of sequentially filtering through membranes from the smallest to largest pore size are Reverse Osmosis (RO), Nanofiltration (NF), Ultrafiltration (UF), and Microfiltration (MF). Filtration with the above-mentioned membranes separates molecules according to their molecular weight by using membranes with specific pore sizes. For example, separation with RO membranes that have pore sizes less than 0.001 micrometers is intended to separate molecules that have a molecular weight less than 200 Daltons. Filtration with NF membranes that have pore sizes from 0.001-0.008 micrometers, inclusive, is intended to separate molecules that have a molecular weight from 200 D to 15 kDa inclusive. Filtration with UF membranes that have 30 pore sizes from 0.005-0.1 micrometers, inclusive, is intended to separate molecules that have a molecular weight from 5 kDa-300 kDa, inclusive. Filtration with microfiltration membranes that have pore sizes from 0.05-3.0 micrometers, inclusive, is intended to separate molecules that have a molecular weight from 100 kDa 3000 kDa and larger. Membrane-filtration can separate the solubilised silk proteins from other components based on size exclusion by utilizing membranes that have a particular Molecular Weight Cut-Off (MQWCO) that is determined by the pore size of the membrane. The MWCO, also called Nominal Molecular Weight Limit (NMWL) or Nominal Molecular Weight Cut-Off (NMWCO), is the kilo Dalton size designation for the filtration by membranes. The MWCO is defined as the molecular weight of the molecule that is 90% retained by the membrane. Because, for example, molecules of the same molecular weight can have significantly different shapes, the MWCO is not an exact metric, but is nevertheless a useful metric and is commonly employed by filter manufacturers. Both hydrophobic as well as hydrophilic membranes may be used. Such membranes may be used as flat sheets or in a spirally wound configuration. Hollow fibres may also be used. In relation to compositions of UF membranes, any number of potential membrane materials may be used including, but not limited to, regenerated cellulose, polyether sulfone (which may or may not be modified to alter its inherent hydrophobicity), polyvinylidene fluoride, and ceramic and metal oxide aggregates. Many polyether sulfone UF membranes can withstand a pH range of 0.5-13, and temperatures ranging 15 up to 85° C. Materials for MF membranes include everything used for UF membranes, as well as polycarbonate, polypropylene, polyethylene and PTFE (TEFLON™). In a preferred embodiment, TFF is used to both concentrate the silk proteins and to alter the buffer composition. Thus, in a preferred embodiment the guanidinium salt concentration is reduced as outlined above and the chemical chaperone, preferably urea, concentration is increased to obtain the above outlined preferred chemical chaperone concentration of the silk protein spinning dope produced in step (d).

In another preferred embodiment phase separation is used to effect concentration of the silk protein solution in step (d). This is based on the phenomenon observed by the present inventors that aqueous silk protein solutions have the tendency to separate into a silk protein enriched aqueous silk protein phase and a silk protein depleted aqueous silk protein phase. The former phase will localize at the bottom of a vessel containing the aqueous silk protein solution resulting from step (c) or from the optional removal step which further removes the denaturant present in a silk protein denaturing concentration in step (a), e.g. the guanidinium salt. To allow phase separation to occur it is preferred that the silk protein solution resulting from the denaturant removal steps is maintained for at least 2 h, preferably for at least 4 h, more preferably for at least 8 h. To facilitate the phase separation minimal disturbance of the solution is preferred.

The aqueous solution of at least one of the steps (a), (b), (c) or (d) may further contain a basic amino acid, i.e. lysine, arginine, or glutamine, preferably arginine. Basic amino acids both have pH buffering capacity and tend to stabilize proteins in solution. It is preferred that the basic amino acid, preferably arginine is comprised at a concentration between 1 mM and 1 M. Preferred concentrations are in the range of 10 mM to 250 mM.

In a preferred embodiment of the first aspect of the invention the method further comprises the step of producing a fibre by drawing the fibre from the silk protein spinning dope solution, by extruding the silk protein spinning dope solution, or by a combination of these two technologies.

"Extrusion" means a process of pushing a solution through a die/opening/nozzle by applying pressure before the die/opening/nozzle. "Drawing" means a process of passing the solution through a die/opening/nozzle by applying pressure after the die/opening/nozzle, whereby the pressure after the die/opening exceed the pressure before the die/opening/nozzle. This can be obtained by drawing gravity, negative pressure or the use of a venturi-nozzle.

The silk protein spinning dope can be spun together with other polymers. Examples include, but are not limited to, polymers (e.g., polypropylene, polyamide, polyester), fibres and silks of other plant and animal sources. A preferred embodiment is silk protein fibre blended with 10% by weight of polyamide. In a further preferred embodiment, the silk protein fibre is blended with polyamide, polyaramide, polylactic acid (PLA), polypropylene, polycaprolactone, polyacrylat, polylactat, polyhydroxybutyrate, polyurethane, xanthan, cellulose, natural and recombinant collagen, keratin, natural and recombinant tropoelastin, elastin, cotton, wool or mixtures thereof. Preferably, the content of this polymer (e.g., polypropylene, polyamide, polyester) in the resulting fibre is less than 50% by weight, more preferably less then 40% by weight, less than 30% by weight, less than 20% by weight and even more preferably less than 15% by weight. Alternatively, it is preferred that the content of this polymer (e.g., polypropylene, polyamide, polyester) in the resulting fibre is at least 5% by weight, at least 10% by weight, at least 15% by weight, at least 20% by weight, at least 30% by weight, at least 40% by weight, or at least 50% by weight, and/or less than 50% by weight, less than 40% by weight, less than 30% by weight, less than 20% by weight, or less than 10% by weight. It is, thus, particularly preferred that the content of this polymer (e.g., polypropylene, polyamide, polyester) in the resulting fibre is in the range of between 5% and 50% by weight, between 5% and 30% by weight, or between 5% and 20% by weight. The production of such combinations of fibres can be readily practiced to enhance any desired characteristics, e.g., appearance, softness, weight, durability, water-repellent properties, improved cost-of-manufacture, that may be generally sought in the manufacture and production of fibres for medical, industrial, or commercial applications. The silk protein fibres can further be bundled, braided or woven with other fibre types.

In a preferred embodiment of the extrusion technology the silk protein spinning dope solution is extruded directly into a coagulation bath, e.g. the spinneret or the die/opening/nozzle may be submerged in a coagulation bath. Similarly, it is possible to immerse the drawn fibre in a coagulation bath after the fibre has formed, e.g. immediately behind the drawing nozzle (the spinneret or the die/opening/nozzle is located above a coagulation bath). The coagulation bath preferably comprises phosphate buffer, and/or alcohols. Preferred alcohols are linear or branched $C_1$ to $C_6$ mono or di-alcohols, preferably ethanol or isopropanol. The concentration of the alcohol(s) in the coagulation bath is preferably in the range of 50 to 100% w/v, e.g. 75% or 90% w/v.

The inventors have discovered that the toughness of the fibre can be significantly improved, if the fibre is extended after drawing or extrusion. Without wishing to be bound by any theory it is believed that the extension leads to an alignment and more regular distribution of the silk protein molecules within the fibre and thereby improves the properties of the fibre. It is preferred that the fibre is extended after it has been drawn or extruded. Such extension can be carried out in a continuous or discontinuous process. In the continuous process it is preferred that the fibre is exposed to a pulling force. Preferably, the extension of the fibre is by at least 2-fold in comparison to the length of the fibre as drawn or extruded, preferably the extension is at least 4-fold, at least 5-fold, at least 6-fold, at least 7-fold, at least 8-fold, and more preferably at least 10-fold. Preferably, such extension is carried out in the presence of the coagulation solution, e.g. the fibre is at least partially submerged in the coagulation solution. This solution is also referred to as stretching solution in the context of the present invention. It has the same composition as the coagulation solution.

The skilled person is well aware of various methods to apply a defined pulling force to achieve the above outlined extension. If, for example, the fibre is drawn or extruded from the nozzle of the spinneret with a speed of 10 cm/s and the fibre is subsequently wound up with a speed of 1 m/s, the extension will be at least 10-fold. The skilled person is well aware of various methods to stretch an extruded fibre in a predetermined way. For example, a roller may be positioned behind the nozzle that draws out the fibre with a speed of 1 m/s the next roller moves with a speed of 2 m/s and subsequent rollers may have an even higher speed, which will lead to an incremental increase of the stretching. The fibre may also be intermittently relaxed to produce a series of stretching and relaxing motions. As outlined above the foldness of extension is calculated on the basis of the fibre as drawn or extruded and the product at the end of the stretching (and possible relaxing) process.

During extension the cross-sectional area of the fibre is reduced. It is preferred that extension leads to a reduction of the cross-sectional area of at least 10%, preferably of at least 20%, of at least 30%, of at least 40%, of at least 50%, 60%, of at least 65%, and more preferably of at least 70%.

The thickness (diameter) of the fibre upon extrusion is preferably in the range of 5 µm to 200 µm and more preferably in the range of 20 µm to 150 µm. Alternatively, the thickness (diameter) of the fibre upon extrusion is preferably in the range of 30 µm to 90 µm and more preferably in the range of 40 µm to 80 µm, or the thickness (diameter) of the fibre upon extrusion is preferably in the range of 110 µm to 200 µm and more preferably in the range of 110 µm to 150 µm. After the extension, the thickness (diameter) of the fibre is preferably in the range of 1 µm to 100 µm and more preferably in the range of 1 µm to 50 µm. Alternatively, the thickness (diameter) of the fibre is preferably in the range of 30 µm to 90 µm and more preferably in the range of 40 µm to 80 µm after the extension. It is preferred that the fibre thickness (diameter) is uniform or has a variation rate of up to 5%, e.g. up to 1%, 2%, 3%, 4%, or 5%. In the latter case, the reference to a fibre thickness (diameter) in the present invention refers to a fibre average thickness (diameter).

In a second aspect the present invention provides a method for producing a fibre comprising the steps:
(i) providing the silk spinning dope solution producible by the method of the first aspect of the invention; and
(ii) producing a fibre by drawing from or extruding or combination thereof the silk protein spinning dope solution.

The provision of the silk spinning dope solution is preferably carried out as described in the context of the first aspect of the invention. In particular it is preferred that the silk protein spinning dope solution is extruded into a coagulation bath.

It is also preferred that the fibre is extended in a subsequent stretching step as outlined regarding the first aspect of the present invention.

In a third aspect the present invention provides a spinning dope solution producible by the method of the first aspect of the invention.

In a fourth aspect the present invention relates to a fibre producible by the method of the first or second aspect of the invention. This fibre exhibits a toughness (measured in MJ/m$^3$) that is superior to the toughness of prior art fibres comprising silk proteins of similar or identical molecular weight. Without wishing to be bound by any theory the inventors believe that this is due to the unique three dimensional structures that the silk proteins can attain if the fibres are drawn from a silk protein spinning dope as provided by the method of the first aspect of the present invention. Preferably, at least 10% by weight of the material of the fibre is (are) silk protein(s). It is more preferred that at least 20%, at least 30%, at least 40%, at least 50%, at least 60%, at least 70%, at least 80%, at least 90%, at least 95% or 100% by weight of the material of the fibre is (are) silk proteins.

If the fibre comprises 100% by weight of silk proteins, it is preferred that these proteins are not naturally occurring silk proteins.

It is also preferred that the silk protein monomer(s) comprised in the fibre has (have) a molecular weight in the range of between 20 kDa to 600 kDa, i.e. at least 20, 25, 30, 35, 40, 45, 50, 55, 60, 65, 70, 75, 80, 85, 90, 95, or 100 kDa or smaller than 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, or 150. It is, thus, particularly preferred that the molecular weight is in the range of 40 kDa to 300 kDa, more preferably 40 kDa to 200 kDa, more preferably, and even more preferably of 100 kDa to 150 kDa.

In cases where the silk protein dimerize, preferably via disulfide bonds in the NR region it is preferred that the another embodiment the molecular weight of the protein dimer is in the range of between 20 kDa to 600 kDa, i.e. at least 20, 25, 30, 35, 40, 45, 50, 55, 60, 65, 70, 75, 80, 85, 90, 95, 100, 110, 120, 130, 140, 150, 160, 170, 180, 190 or 200 kD or smaller than 600, 590, 580, 570, 560, 550, 540, 530, 520, 510, 500, 490, 480, 470, 460, 450, 440, 430, 420, 410, 400, 390, 380, 370, 360, 350, 340, 330, 320, 310 or 300, most preferably between 200 kDa to 300 kD. Preferably, the fibre has a toughness (MJ/m$^3$) that is the product of the molecular weight of the silk protein(s) in kDa and a factor of at least 1.0. This relation is obtained at least up to a molecular weight of the silk protein(s) of 300 kDa and is at least 300 MJ/m$^3$ for proteins with a molecular weight of above 300 kDa. Preferably, the factor is at least 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0.

If the silk protein solution comprises more than one silk protein the molecular weight of the silk proteins for the purpose of this calculation is determined by the molecular weight of the silk protein with the lowest molecular weight.

For the purpose of calculating the molecular weight of the silk proteins comprised in the silk protein solution in cases wherein the silk proteins are capable of dimerizing through covalent bonds, e.g. disulfide bonds between two Cys residues, the weight of the non-dimerized monomer is used. Thus, fibres of the invention, which comprise dimers with a molecular weight of 200 kD, the toughness is calculated on the basis of the molecular weight of the monomers forming the dimers, i.e. 100 kD. Thus, in the example the fibre has a toughness of at least 100 MJ/m$^3$.

The fibre is preferably extended. It is preferred that the extension is by at least 2-fold in comparison to the length of the fibre as drawn or extruded, preferably the extension is at least 4-fold, at least 5-fold, at least 6-fold, at least 7-fold, at least 8-fold, and more preferably at least 10-fold.

During extension the cross-sectional area of the fibre is reduced. It is preferred that extension leads to a reduction of the cross-sectional area of at least 10%, preferably of at least 20%, of at least 30%, of at least 40%, of at least 50%, 60%, of at least 65%, and more preferably of at least 70%.

The thickness (diameter) of the fibre upon extrusion is preferably in the range of 5 µm to 200 µm and more preferably in the range of 20 µm to 150 µm. Alternatively, the thickness (diameter) of the fibre upon extrusion is preferably in the range of 30 µm to 90 µm and more preferably in the range of 40 µm to 80 µm, or the thickness (diameter) of the fibre upon extrusion is preferably in the range of 110 µm to 200 µm and more preferably in the range of 110 µm to 150 µm. After the extension, the thickness (diameter) of the fibre is preferably in the range of 1 µm to 100 µm and more preferably in the range of 1 µm to 50 µm. Alternatively, the thickness (diameter) of the fibre is preferably in the range of 30 µm to 90 µm and more preferably in the range of 40 µm to 80 µm after the extension. It is preferred that the fibre thickness (diameter) is uniform or has a variation rate of up to 5%, e.g. up to 1%, 2%, 3%, 4%, or 5%. In the latter case, the reference to a fibre thickness (diameter) in the present invention refers to a fibre average thickness (diameter).

In a fifth aspect the present invention relates to a fibre comprising at least one silk protein, wherein at least 10% by weight of the material of the fibre is(are) silk protein(s), wherein the silk protein monomer(s) has have a molecular weight in the range of 20 kDa to 600 kDa and the fibre has a toughness (MJ/m$^3$) that is the product of the molecular weight of the silk protein(s) in kDa and the factor of at least 1.0 at least up to an molecular weight of the silk protein(s) of 300 kDa and is at least 300 MJ/m$^3$ for proteins with an molecular weight of above 300 kDa.

Preferably, the factor is at least 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0.

It is more preferred that at least 20%, at least 30%, at least 40%, at least 50%, at least 60%, at least 70%, at least 80%, at least 90%, at least 95% or 100% by weight of the material of the fibre is (are) silk proteins.

If the fibre comprises 100% by weight of silk proteins, it is preferred that these proteins are not naturally occurring silk proteins.

The silk proteins that may be comprised in the fibre according to the fifth aspect of the invention are those described as suitable in the context of the first aspect of the invention, including all the preferred and particularly preferred embodiments. Accordingly, it is preferred that the silk protein comprises 2 to 100 repetitive units, i.e. at least 2, 3, 4, 5, 6, 7, 8, 9, 10, 11, 12, 13, 14, 15, 16, 17, 18, 19, 20, 21, 22, 23, 24, 25, 26, 27, 28, 29, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more repetitive units.

It is particularly preferred that the silk protein comprises at least two repetitive units each comprising at least one consensus sequence selected from the group consisting of:
(a) GPGXX (SEQ ID NO: 3), wherein X is any amino acid, preferably in each case independently selected from the A, S, G, Y, P, and Q;
(b) GGX, wherein X is any amino acid, preferably in each case independently selected from Y, P, R, S, A, T, N and Q; and
(c) $A_x$, wherein x is an integer from 5 to 10.

Preferably, the repetitive units are independently selected from module A (SEQ ID NO: 20), module C (SEQ ID NO: 21), module Q (SEQ ID NO: 22), module S (SEQ ID NO: 25), module R(SEQ ID NO: 26), or variants thereof.

For example, the silk protein comprises 2 to 100 repetitive units, i.e. at least 2, 3, 4, 5, 6, 7, 8, 9, 10, 11, 12, 13, 14, 15, 16, 17, 18, 19, 20, 21, 22, 23, 24, 25, 26, 27, 28, 29, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more repetitive units, wherein the repetitive units are independently selected from module A (SEQ ID NO: 20), module C (SEQ ID NO: 21), module Q (SEQ ID NO: 22), module S (SEQ ID NO: 25), module R(SEQ ID NO: 26), or variants thereof.

Preferably, the silk protein further comprises at least one non-repetitive (NR) unit.

Preferred NR units are NR3 (SEQ ID NO: 41), NR4 (SEQ ID NO: 42), NR5 (SEQ ID NO: 45) or NR6 (SEQ ID NO: 46) or variants thereof.

The silk protein may be selected from the group consisting of ADF-3 (SEQ ID NO: 1), ADF-4 (SEQ ID NO: 2), MaSp I (SEQ ID NO: 43), or MaSp II (SEQ ID NO: 44); or variants thereof; or $(C)_m NR_z$, $NR_z(C)_m$, $NR_z(C)_m NR_z$, $(AQ)_n NR_z$, $NR_z(AQ)_n$, $NR_z(AQ)_n NR_z$, $(NR_z QAQ)_o$, $(QAQ)_o NR_z$, wherein m is an integer of 10 to 64, i.e. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60; n is an integer of 10 to 40, i.e. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40; o is an integer of 8 to 40, i.e. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40; and z is an integer of 1 to 3,i.e. 1, 2 or 3, preferably 1 and NR in each case independently is a non-repetitive unit.

The silk protein is preferably $C_8NR4$, $C_{16}NR4$, $C_{32}NR4$, $(AQ)_{12}NR3$, $(AQ)_{24}NR3$, $((AQ)_{24}C32$, $NR4C_{16}NR4$, $NR4C_{32}NR4$, $NR3C_{16}NR3$, $NR3C_{32}NR3$, $NR4(AQ)_{12}NR4$, $NR4(AQ)_{24}NR4$, $NR3(AQ)_{12}NR3$, $NR3$ $(AQ)_{24}NR3$, $(QAQ)_{16}$, $NR5C_{16}NR4$, $NR6C_{16}NR4$, $NR5C_{32}NR4$, $NR6C_{32}NR4$, $NR5C_{16}NR3$, $NR6C_{16}NR3$, $NR5C_{32}NR3$, $NR6C_{16}NR3$, $NR5(AQ)_{12}NR4$, $NR6(AQ)_{12}NR4$, $NR5(AQ)_{24}NR4$, $NR6(AQ)_{24}NR4$, $NR5(AQ)_{12}NR3$, $NR6(AQ)_{12}NR3$, $NR5(AQ)_{24}NR3$, $NR6(AQ)_{24}NR3$.

The fibre is preferably extended. It is preferred that the extension is by at least 2-fold in comparison to the length of the fibre as drawn or extruded, preferably the extension is at least 4-fold, at least 5-fold, at least 6-fold, at least 7-fold, at least 8-fold, and more preferably at least 10-fold. The extension significantly improves the toughness of the fibre.

The thickness (diameter) of the fibre upon extrusion is preferably in the range of 5 μm to 200 μm and more preferably in the range of 20 μm to 150 μm. Alternatively, the thickness (diameter) of the fibre upon extrusion is preferably in the range of 30 μm to 90 μm and more preferably in the range of 40 μm to 80 μm, or the thickness (diameter) of the fibre upon extrusion is preferably in the range of 110 μm to 200 μm and more preferably in the range of 110 μm to 150 μm. After the extension, the thickness (diameter) of the fibre is preferably in the range of 1 μm to 100 μm and more preferably in the range of 1 μm to 50 μm. Alternatively, the thickness (diameter) of the fibre is preferably in the range of 30 μm to 90 μm and more preferably in the range of 40 μm to 80 μm after the extension. It is preferred that the fibre thickness (diameter) is uniform or has a variation rate of up to 5%, e.g. up to 1%, 2%, 3%, 4%, or 5%. In the latter case, the reference to a fibre thickness (diameter) in the present invention refers to a fibre average thickness (diameter).

The fibre of the fourth or fifth aspect of the invention may further comprise at least one additional polymer. For example, the fibre of the fourth or fifth aspect of the invention may comprise a synthetic and/or natural polymer. Preferred polymers comprise artificial and/or naturally occurring polymers including polyamide, polycaprolactone, polyacrylate, polylactate, polyhydroxybutyrate, polyurethane, xanthan, cellulose, collagen, tropoelastin, elastin, keratin, cotton, wool or mixtures thereof. Preferably, the content of the at least one additional polymer, e.g. synthetic and/or natural polymer, in the fibre is less than 50% by weight, more preferably less then 40% by weight, less than 30% by weight, less than 20% by weight and even more preferably less than 15% by weight. Alternatively, it is preferred that the content of the at least one additional polymer, e.g. synthetic and/or natural polymer, in the fibre is at least 5% by weight, at least 10% by weight, at least 15% by weight, at least 20% by weight, at least 30% by weight, at least 40% by weight, or at least 50% by weight, and/or less than 50% by weight, less than 40% by weight, less than 30% by weight, less than 20% by weight, or less than 10% by weight. It is, thus, particularly preferred that the content of the at least one additional polymer, e.g. synthetic and/or natural polymer, in the fibre is in the range of between 5% and 50% by weight, between 5% and 30% by weight, or between 5% and 20% by weight. The production of such fibre can be readily practiced to enhance any desired characteristics, e.g., appearance, softness, weight, durability, water-repellent properties, improved cost-of-manufacture, that may be generally sought in the manufacture and production of fibres for medical, industrial, or commercial applications. The silk protein fibres can further be bundled, braided or woven with other fibre types.

As mentioned above, it is more preferred that at least 20%, at least 30%, at least 40%, at least 50%, at least 60%, at least 70%, at least 80%, at least 90%, at least 95% or 100% by weight of the material of the fibre is (are) silk protein(s). It is even more preferred that at least 10% by weight of the material of the fibre is (are) silk protein(s) and no more than 90% by weight of the material of the fibre is another polymer, e.g. synthetic or natural polymer, at least 20% by weight of the material of the fibre is (are) silk protein(s) and no more than 80% by weight of the material of the fibre is another polymer, e.g. synthetic or natural polymer, at least 30% by weight of the material of the fibre is (are) silk protein(s) and no more than 70% by weight of the material of the fibre is another polymer, e.g. synthetic or natural polymer, at least 40% by weight of the material of the fibre is (are) silk protein(s) and no more than 60% by weight of the material of the fibre is another polymer, e.g. synthetic or natural polymer, at least 50% by weight of the material of the fibre is (are) silk protein(s) and no more than 50% by weight of the material of the fibre is another polymer, e.g. synthetic or natural polymer, at least 60% by weight of the material of the fibre is (are) silk protein(s) and no more than 40% by weight of the material of the fibre is another polymer, e.g. synthetic or natural polymer, at least 70% by weight of the material of the fibre is (are) silk protein(s) and no more than 30% by weight of the material of the fibre is another polymer, e.g. synthetic or natural polymer, at least 80% by weight of the material of the fibre is (are) silk protein(s) and no more than 20% by weight of the material of the fibre is another material, e.g. synthetic or natural polymer, at least 90% by weight of the material of the fibre is (are) silk protein(s) and no more than 10% by weight of the material of the fibre is another polymer, e.g. synthetic or natural polymer, or at least 95% by weight of the material of the fibre is (are) silk protein(s) and no more than 5% by weight of the material of the fibre is another polymer, e.g. synthetic or natural polymer.

EXAMPLES

Spinning Process:
1. Preparation of the spinning dope 500 mg of the recombinant spider silk protein ($C_{16}NR4$, $C_{32}NR4$, $(AQ)_{12}NR3$, $NR5(AQ)_{12}NR3$, or $(AQ)_{24}NR3$)) was dissolved in 10 mL of 6 M GdmSCN (5% (w/v)). After the protein was dissolved, insoluble parts were removed by centrifuging (8500 rpm, 30 min, 18° C.). The supernatant was dialyzed (MWCO: 6-8 kDa) each time for 4 hours with the following buffers:

1) Buffer 1: 50 mM $NH_4HCO_3$ (pH 7.8), 500 mM urea, 500 mM GdmSCN
2) Buffer 2: 50 mM $NH_4HCO_3$ (pH 7.8), 500 mM urea, 250 mM GdmSCN
3) Buffer 3: 50 mM $NH_4HCO_3$ (pH 7.8), 500 mM urea As a next step eADF4 C-proteins ($C_{16}NR4$, C32NR4) were handled differently than eADF3 AQ-proteins ($(AQ)_{12}NR3$, $NR5(AQ)_{12}NR3$, $(AQ)_{24}NR3$):

C-proteins: dialysis against 20% (w/v) PEG (35 kDa), 500 mM urea until a concentration of 15% is reached. The spinning dope can now be used for spinning AQ-proteins: transfer to 15 mL Greiner tubes. The tubes were kept at 4° C. overnight, where phase separation takes place. The concentrated (lower) phase (9-15% (w/v)) was used for spinning 2. Wet-Spinning The spinning dope was transferred into a 1 mL syringe with a 22G cannula. The filled syringe was mounted on a syringe pump. The cannula was bent down perpendicular to the syringe so that the tip of the cannula is submerged into the coagulation bath Coagulation/Stretching Baths:

C-proteins: 90% Isopropanol, 10% $H_2O$

AQ-proteins: 75% Isopropanol, 25% $H_2O$,

The spinning dope was extruded into the coagulation bath with a spinning speed of 5 µL/min. The coagulated fiber was taken out of the bath and was stretched in a stretching bath. Coagulation and stretching bath are identical for the respective C- or AQ-protein. After stretching, the fibers were taken out of the stretching bath and placed in a clean petri dish to dry in open air for at least 2 h.

3. Tensile Testing

For tensile tests, the dried fibers were cut into 1 cm fragments, which were glued onto plastic frames (gauge length: 2 mm) using plastic glue. The glued fiber-fragments were air-dried overnight. The diameter of the fiber-fragments was determined with a light microscope (100-fold, 200-fold and 400-fold magnification) at three points distributed evenly throughout the fiber-fragment.

Afterwards, stress-strain curves were recorded on a tensile tester with a 0.5 N load cell at a relative humidity of 30%. The fibers were extended with a rate of 0.04 mm/s until they ruptured. The results are shown in Table 1

TABLE 1

Experimental results of different spider silk proteins. The table further shows a comparison to experimental data regarding four recombinant spider silk protein fibers described in Xia et al. (2010) Native-sized recombinant spider silk protein produced in metabolically engineered *Escherichia coli* results in a strong fiber. PNAS August 10, 2010 Vol. 107 no. 3214059-14063.

|  | Protein | Stretching [%] | Diameter [µm] | Extensibility [%] | Strength [MPa] | Toughness [MJ/m$^3$] | Young's modulus [GPa] |
|---|---|---|---|---|---|---|---|
| eADF4 | $C_{16}NR4$ | 300 | 23 | 76 | 366 | 162.8 | 1.4 |
|  | 56 kDa monomer |  |  |  |  |  |  |
|  | $C_{32}NR4$ |  |  |  |  | 254.0 |  |
|  | 104 kDa monomer |  |  |  |  |  |  |

TABLE 1-continued

Experimental results of different spider silk proteins. The table further shows a comparison to experimental data regarding four recombinant spider silk protein fibers described in Xia et al. (2010) Native-sized recombinant spider silk protein produced in metabolically engineered *Escherichia coli* results in a strong fiber. PNAS August 10, 2010 Vol. 107 no. 3214059-14063.

|  | Protein | Stretching [%] | Diameter [µm] | Extensibility [%] | Strength [MPa] | Toughness [MJ/m³] | Young's modulus [GPa] |
|---|---|---|---|---|---|---|---|
| eADF3 | (AQ)₁₂NR3 58 kDa monomer | 500 | 47 ± 4 | 124.6 ± 47.5 | 206.8 ± 56.4 | 97.4 ± 37 | 2.5 ± 0.4 |
|  | NR5 (AQ)₁₂NR3 72 kDa monomer | 600 | 22 ± 1 | 59.5 ± 22.5 | 350.0 ± 39.0 | 98.4 ± 41.0 | 4.2 ± 0.2 |
|  | (AQ)₂₄NR3 106 kDa monomer | 600 | 14 ± 2 | 118.2 ± 29.2 | 205.9 ± 39.3 | 150.0 ± 49.9 | 2.2 ± 0.7 |
| Xia et al. (*) | 16-mer 54 kDa |  |  | 2.5 | 70 | 1 |  |
|  | 32-mer 100 kDa |  |  | 3 | 200 | 3 |  |
|  | 64-mer 192 kDa |  |  | 5 | 270 | 10 | 10 |
|  | 96-mer 284 kDa |  |  | 20 | 600 | 141 | 23 |

(*) The data regarding toughness were calculated on the basis of FIG. 3 of Xia et. al (supra).

---

The invention claimed is:

1. Fibre comprising at least one silk protein, wherein at least 10% by weight of the fibre is (are) silk protein(s), wherein the silk protein monomer(s) has(have) a molecular weight in the range of 20 kDa to 600 kDa and the fibre has a toughness (MJ/m$^3$) that is the product of the molecular weight of the silk protein(s) in kDa and the factor of at least 1.0 to a molecular weight of the silk protein(s) of 300 kDa and is at least 300 MJ/m$^3$ for proteins with a molecular weight of above 300 kDa;
   wherein the silk protein comprises at least two repetitive units each comprising at least one consensus sequence selected from the group consisting of:
   (a) GPGXX (SEQ ID NO: 3), wherein X is in each case independently selected from the amino acids A, S, G, Y, P, and Q;
   (b) GGX, wherein X is in each case independently selected from the amino acids Y, P, R, S, A, T, N and Q; and
   (c) A$_x$, wherein A is an amino acid and x is an integer from 5 to 10; and,
   wherein the repetitive units are selected from the group consisting of module A (SEQ ID NO: 20) or a variant thereof, module C (SEQ ID NO: 21) or a variant thereof, and module Q (SEQ ID NO: 22) or a variant thereof;
   wherein the variant of module A (SEQ ID NO: 20) has a sequence identity of at least 90% to said module, the variant of module C (SEQ ID NO: 21) has a sequence identity of at least 90% to said module, and the variant of module Q (SEQ ID NO: 22) has a sequence identity of at least 90% to said module.

2. The fibre of claim 1, wherein the silk protein further comprises at least one non-repetitive (NR) unit.

3. The fibre of claim 2, wherein the NR unit is NR3 (SEQ ID NO: 41), NR4 (SEQ ID NO: 42), NR5 (SEQ ID NO: 45) or NR6 (SEQ ID NO: 46) or variants thereof.

4. The fibre of claim 1, wherein the fibre further comprises a synthetic or natural polymer.

5. The fibre of claim 4, wherein the polymer is polyamide, polycaprolactone, polyacrylate, polyaramide, polylactic acid (PLA), polypropylene, polylacetate, polyhydroxybutyrate, polyurethane, xanthan, cellulose, collagen, tropoelastin, elastin, keratin, cotton, wool or mixtures thereof.

6. The fibre of claim 1, wherein the at least two repetitive units are module C (SEQ ID NO: 21) or a variant thereof, wherein the variant of module C (SEQ ID NO: 21) has a sequence identity of at least 90% to said module.

7. The fibre of claim 1, wherein the at least two repetitive units are module A (SEQ ID NO: 20) or a variant thereof and module Q (SEQ ID NO: 22) or a variant thereof,
   wherein module A (SEQ ID NO: 20) or a variant thereof is combined with module Q (SEQ ID NO: 22) or a variant thereof, and
   wherein the variant of module A (SEQ ID NO: 20) has a sequence identity of at least 90% to said module and the variant of module Q (SEQ ID NO: 22) has a sequence identity of at least 90% to said module.

* * * * *

SEQUENCE LISTING

<160> NUMBER OF SEQ ID NOS: 46

<210> SEQ ID NO 1
<211> LENGTH: 636
<212> TYPE: PRT
<213> ORGANISM: Araneus diadematus
<220> FEATURE:
<221> NAME/KEY: PEPTIDE
<222> LOCATION: (1)..(636)
<223> OTHER INFORMATION: ADF-3

<400> SEQUENCE: 1

Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
                20                  25                  30

Ala Ala Ala Ala Ala Gly Gly Tyr Gly Pro Gly Ser Gly Gln Gln Gly
            35                  40                  45

Pro Ser Gln Gln Gly Pro Gly Gln Gln Gly Pro Gly Gly Gln Gly Pro
        50                  55                  60

Tyr Gly Pro Gly Ala Ser Ala Ala Ala Ala Ala Gly Gly Tyr Gly
65                  70                  75                  80

Pro Gly Ser Gly Gln Gln Gly Pro Gly Gly Gln Gly Pro Tyr Gly Pro
                85                  90                  95

Gly Ser Ser Ala Ala Ala Ala Ala Gly Gly Asn Gly Pro Gly Ser
                100                 105                 110

Gly Gln Gln Gly Ala Gly Gln Gln Gly Pro Gly Gln Gln Gly Pro Gly
            115                 120                 125

Ala Ser Ala Ala Ala Ala Ala Gly Gly Tyr Gly Pro Gly Ser Gly
        130                 135                 140

Gln Gln Gly Pro Gly Gln Gln Gly Pro Gly Gln Gly Pro Tyr Gly
145                 150                 155                 160

Pro Gly Ala Ser Ala Ala Ala Ala Ala Gly Gly Tyr Gly Pro Gly
                165                 170                 175

Ser Gly Gln Gly Pro Gly Gln Gln Gly Pro Gly Gln Gly Pro Tyr

```
            180                 185                 190
Gly Pro Gly Ala Ser Ala Ala Ala Ala Ala Gly Gly Tyr Gly Pro
        195                 200                 205
Gly Ser Gly Gln Gln Gly Pro Gly Gln Gln Gly Pro Gly Gln Gly
    210                 215                 220
Pro Gly Gly Gln Gly Pro Tyr Gly Pro Gly Ala Ser Ala Ala Ala
225                 230                 235                 240
Ala Ala Gly Gly Tyr Gly Pro Gly Tyr Gly Gln Gln Gly Pro Gly Gln
                245                 250                 255
Gln Gly Pro Gly Gly Gln Gly Pro Tyr Gly Pro Gly Ala Ser Ala Ala
            260                 265                 270
Ser Ala Ala Ser Gly Gly Tyr Gly Pro Gly Ser Gly Gln Gln Gly Pro
        275                 280                 285
Gly Gln Gln Gly Pro Gly Gln Gly Pro Tyr Gly Pro Gly Ala Ser
    290                 295                 300
Ala Ala Ala Ala Ala Ala Gly Gly Tyr Gly Pro Gly Ser Gly Gln Gln
305                 310                 315                 320
Gly Pro Gly Gln Gln Gly Pro Gly Gln Gln Gly Pro Gly Gln Gln Gly
                325                 330                 335
Pro Gly Gly Gln Gly Pro Tyr Gly Pro Gly Ala Ser Ala Ala Ala Ala
            340                 345                 350
Ala Ala Gly Gly Tyr Gly Pro Gly Ser Gly Gln Gln Gly Pro Gly Gln
        355                 360                 365
Gln Gly Pro Gly Gln Gln Gly Pro Gly Gln Gln Gly Pro Gly Gln Gln
    370                 375                 380
Gly Pro Gly Gln Gln Gly Pro Gly Gln Gln Gly Pro Gly Gln Gln Gly
385                 390                 395                 400
Pro Gly Gln Gln Gly Pro Gly Gln Gly Ala Tyr Gly Pro Gly Ala
                405                 410                 415
Ser Ala Ala Ala Gly Ala Ala Gly Gly Tyr Gly Pro Gly Ser Gly Gln
            420                 425                 430
Gln Gly Pro Gly Gln Gln Gly Pro Gly Gln Gln Gly Pro Gly Gln Gln
        435                 440                 445
Gly Pro Gly Gln Gln Gly Pro Gly Gln Gln Gly Pro Gly Gln Gln Gly
    450                 455                 460
Pro Gly Gln Gln Gly Pro Tyr Gly Pro Gly Ala Ser Ala Ala Ala Ala
465                 470                 475                 480
Ala Ala Gly Gly Tyr Gly Pro Gly Ser Gly Gln Gln Gly Pro Gly Gln
                485                 490                 495
Gln Gly Pro Gly Gln Gln Gly Pro Gly Gln Gly Pro Tyr Gly Pro
            500                 505                 510
Gly Ala Ala Ser Ala Ala Val Ser Val Gly Gly Tyr Gly Pro Gln Ser
        515                 520                 525
Ser Val Pro Val Ala Ser Ala Val Ala Ser Arg Leu Ser Ser Pro
    530                 535                 540
Ala Ala Ser Ser Arg Val Ser Ser Ala Val Ser Ser Leu Val Ser Ser
545                 550                 555                 560
Gly Pro Thr Lys His Ala Ala Leu Ser Asn Thr Ile Ser Ser Val Val
                565                 570                 575
Ser Gln Val Ser Ala Ser Asn Pro Gly Leu Ser Gly Cys Asp Val Leu
            580                 585                 590
Val Gln Ala Leu Leu Glu Val Val Ser Ala Leu Val Ser Ile Leu Gly
        595                 600                 605
```

```
Ser Ser Ser Ile Gly Gln Ile Asn Tyr Gly Ala Ser Ala Gln Tyr Thr
    610                 615                 620

Gln Met Val Gly Gln Ser Val Ala Gln Ala Leu Ala
625                 630                 635

<210> SEQ ID NO 2
<211> LENGTH: 410
<212> TYPE: PRT
<213> ORGANISM: Araneus diadematus
<220> FEATURE:
<221> NAME/KEY: PEPTIDE
<222> LOCATION: (1)..(410)
<223> OTHER INFORMATION: ADF-4

<400> SEQUENCE: 2

Ala Gly Ser Ser Ala Ala Ala Ala Ala Ser Gly Ser Gly Gly
1               5                   10                  15

Tyr Gly Pro Glu Asn Gln Gly Pro Ser Gly Pro Val Ala Tyr Gly Pro
                20                  25                  30

Gly Gly Pro Val Ser Ser Ala Ala Ala Ala Ala Gly Ser Gly
        35                  40                  45

Pro Gly Gly Tyr Gly Pro Glu Asn Gln Gly Pro Ser Gly Pro Gly Gly
50                  55                  60

Tyr Gly Pro Gly Ser Gly Ser Ser Ala Ala Ala Ala Ala Ala
65              70                  75                  80

Ala Ser Gly Pro Gly Gly Tyr Gly Pro Gly Ser Gln Gly Pro Ser Gly
                85                  90                  95

Pro Gly Gly Ser Gly Gly Tyr Gly Pro Gly Ser Gln Gly Ala Ser Gly
                100                 105                 110

Pro Gly Gly Pro Gly Ala Ser Ala Ala Ala Ala Ala Ala Ala
                115                 120                 125

Ala Ser Gly Pro Gly Gly Tyr Gly Pro Gly Ser Gln Gly Pro Ser Gly
                130                 135                 140

Pro Gly Ala Tyr Gly Pro Gly Gly Pro Gly Ser Ser Ala Ala Ala Ala
145                 150                 155                 160

Ala Ala Ala Ala Ser Gly Pro Gly Gly Tyr Gly Pro Gly Ser Gln Gly
                165                 170                 175

Pro Ser Gly Pro Gly Val Tyr Gly Pro Gly Gly Pro Gly Ser Ser Ala
                180                 185                 190

Ala Ala Ala Ala Ala Gly Ser Gly Pro Gly Gly Tyr Gly Pro Glu
                195                 200                 205

Asn Gln Gly Pro Ser Gly Pro Gly Gly Tyr Gly Pro Gly Gly Ser Gly
                210                 215                 220

Ser Ser Ala Ala Ala Ala Ala Ala Ala Ser Gly Pro Gly Gly Tyr
225                 230                 235                 240

Gly Pro Gly Ser Gln Gly Pro Ser Gly Pro Gly Gly Ser Gly Gly Tyr
                245                 250                 255

Gly Pro Gly Ser Gln Gly Gly Ser Gly Pro Gly Ala Ser Ala Ala Ala
                260                 265                 270

Ala Ala Ala Ala Ala Ser Gly Pro Gly Gly Tyr Gly Pro Gly Ser Gln
                275                 280                 285

Gly Pro Ser Gly Pro Gly Tyr Gln Gly Pro Ser Gly Pro Gly Ala Tyr
                290                 295                 300

Gly Pro Ser Pro Ser Ala Ser Ala Ser Val Ala Ala Ser Val Tyr Leu
305                 310                 315                 320
```

```
Arg Leu Gln Pro Arg Leu Glu Val Ser Ser Ala Val Ser Ser Leu Val
                325                 330                 335

Ser Ser Gly Pro Thr Asn Gly Ala Ala Val Ser Gly Ala Leu Asn Ser
            340                 345                 350

Leu Val Ser Gln Ile Ser Ala Ser Asn Pro Gly Leu Ser Gly Cys Asp
        355                 360                 365

Ala Leu Val Gln Ala Leu Leu Glu Leu Val Ser Ala Leu Val Ala Ile
    370                 375                 380

Leu Ser Ser Ala Ser Ile Gly Gln Val Asn Val Ser Ser Val Ser Gln
385                 390                 395                 400

Ser Thr Gln Met Ile Ser Gln Ala Leu Ser
                405                 410

<210> SEQ ID NO 3
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(5)
<223> OTHER INFORMATION: consensus peptide motif

<400> SEQUENCE: 3

Gly Pro Gly Xaa Xaa
1               5

<210> SEQ ID NO 4
<211> LENGTH: 5
<212> TYPE: PRT
<213> ORGANISM: Araneus diadematus
<220> FEATURE:
<221> NAME/KEY: VARIANT
<222> LOCATION: (4)..(4)
<223> OTHER INFORMATION: Q at position 4 may also be alanine, serine,
      glycine, tyrosine, proline, or glutamine
<220> FEATURE:
<221> NAME/KEY: VARIANT
<222> LOCATION: (5)..(5)
<223> OTHER INFORMATION: Q at position 5 may also be alanine, serine,
      glycine, tyrosine, proline, or glutamine

<400> SEQUENCE: 4

Gly Pro Gly Gln Gln
1               5

<210> SEQ ID NO 5
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-3)

<400> SEQUENCE: 5

Gly Pro Gly Ala Ser
1               5

<210> SEQ ID NO 6
<211> LENGTH: 5
<212> TYPE: PRT
<213> ORGANISM: Araneus diadematus
<220> FEATURE:
<221> NAME/KEY: REPEAT
<222> LOCATION: (1)..(5)
```

```
<223> OTHER INFORMATION: peptide motif (ADF-3)

<400> SEQUENCE: 6

Gly Pro Gly Ser Gly
1               5

<210> SEQ ID NO 7
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-4)

<400> SEQUENCE: 7

Gly Pro Gly Gly Tyr
1               5

<210> SEQ ID NO 8
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-4)

<400> SEQUENCE: 8

Gly Pro Gly Gly Pro
1               5

<210> SEQ ID NO 9
<211> LENGTH: 5
<212> TYPE: PRT
<213> ORGANISM: Nephila clavipes
<220> FEATURE:
<221> NAME/KEY: REPEAT
<222> LOCATION: (1)..(5)
<223> OTHER INFORMATION: peptide motif (flagelliform protein)

<400> SEQUENCE: 9

Gly Pro Gly Gly Ala
1               5

<210> SEQ ID NO 10
<211> LENGTH: 5
<212> TYPE: PRT
<213> ORGANISM: Arthropoda
<220> FEATURE:
<221> NAME/KEY: REPEAT
<222> LOCATION: (1)..(5)
<223> OTHER INFORMATION: peptide motif (resilin)

<400> SEQUENCE: 10

Gly Pro Gly Gly Gly
1               5

<210> SEQ ID NO 11
<211> LENGTH: 5
<212> TYPE: PRT
<213> ORGANISM: Nephila clavipes
<220> FEATURE:
<221> NAME/KEY: REPEAT
<222> LOCATION: (1)..(5)
<223> OTHER INFORMATION: peptide motif (flagelliform protein)

<400> SEQUENCE: 11
```

```
Gly Pro Gly Gly Ser
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(5)
<223> OTHER INFORMATION: Ax peptide motif

<400> SEQUENCE: 12

Ala Ala Ala Ala Ala
1               5

<210> SEQ ID NO 13
<211> LENGTH: 6
<212> TYPE: PRT
<213> ORGANISM: Araneus diadematus
<220> FEATURE:
<221> NAME/KEY: REPEAT
<222> LOCATION: (1)..(6)
<223> OTHER INFORMATION: Ax peptide motif (ADF 3)

<400> SEQUENCE: 13

Ala Ala Ala Ala Ala Ala
1               5

<210> SEQ ID NO 14
<211> LENGTH: 7
<212> TYPE: PRT
<213> ORGANISM: Araneus diadematus
<220> FEATURE:
<221> NAME/KEY: REPEAT
<222> LOCATION: (1)..(7)
<223> OTHER INFORMATION: Ax peptide motif (ADF-4)

<400> SEQUENCE: 14

Ala Ala Ala Ala Ala Ala Ala
1               5

<210> SEQ ID NO 15
<211> LENGTH: 8
<212> TYPE: PRT
<213> ORGANISM: Araneus diadematus
<220> FEATURE:
<221> NAME/KEY: REPEAT
<222> LOCATION: (1)..(8)
<223> OTHER INFORMATION: Ax peptide motif (ADF-4)

<400> SEQUENCE: 15

Ala Ala Ala Ala Ala Ala Ala Ala
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(9)
<223> OTHER INFORMATION: Ax peptide motif

<400> SEQUENCE: 16
```

Ala Ala Ala Ala Ala Ala Ala Ala Ala
1               5

<210> SEQ ID NO 17
<211> LENGTH: 10
<212> TYPE: PRT
<213> ORGANISM: Araneus diadematus
<220> FEATURE:
<221> NAME/KEY: REPEAT
<222> LOCATION: (1)..(10)
<223> OTHER INFORMATION: Ax peptide motif (ADF-4)

<400> SEQUENCE: 17

Ala Ala Ala Ala Ala Ala Ala Ala Ala Ala
1               5                   10

<210> SEQ ID NO 18
<211> LENGTH: 9
<212> TYPE: PRT
<213> ORGANISM: Arthropoda
<220> FEATURE:
<221> NAME/KEY: REPEAT
<222> LOCATION: (1)..(9)
<223> OTHER INFORMATION: peptide motif (based on resilin)

<400> SEQUENCE: 18

Gly Gly Arg Pro Ser Asp Thr Tyr Gly
1               5

<210> SEQ ID NO 19
<211> LENGTH: 9
<212> TYPE: PRT
<213> ORGANISM: Arthropoda
<220> FEATURE:
<221> NAME/KEY: REPEAT
<222> LOCATION: (1)..(9)
<223> OTHER INFORMATION: peptide motif (based on resilin)

<400> SEQUENCE: 19

Gly Gly Arg Pro Ser Ser Ser Tyr Gly
1               5

<210> SEQ ID NO 20
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module A (ADF-3)

<400> SEQUENCE: 20

Gly Pro Tyr Gly Pro Gly Ala Ser Ala Ala Ala Ala Ala Ala Gly Gly
1               5                   10                  15

Tyr Gly Pro Gly Ser Gly Gln Gln
            20

<210> SEQ ID NO 21
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module C (ADF-4)

-continued

<400> SEQUENCE: 21

Gly Ser Ser Ala Ala Ala Ala Ala Ala Ala Ser Gly Pro Gly Gly
1               5                   10                  15

Tyr Gly Pro Glu Asn Gln Gly Pro Ser Gly Pro Gly Tyr Gly Pro
            20                  25                  30

Gly Gly Pro
        35

<210> SEQ ID NO 22
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(20)
<223> OTHER INFORMATION: Module Q (ADF-3)

<400> SEQUENCE: 22

Gly Pro Gly Gln Gln Gly Pro Gly Gln Gln Gly Pro Gly Gln Gln Gly
1               5                   10                  15

Pro Gly Gln Gln
            20

<210> SEQ ID NO 23
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(4)
<223> OTHER INFORMATION: peptide linker

<400> SEQUENCE: 23

Gly Gly Cys Gly
1

<210> SEQ ID NO 24
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(4)
<223> OTHER INFORMATION: peptide linker

<400> SEQUENCE: 24

Gly Cys Gly Gly
1

<210> SEQ ID NO 25
<211> LENGTH: 34
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(34)
<223> OTHER INFORMATION: Module S (Resilin)

<400> SEQUENCE: 25

```
Pro Gly Ser Ser Ala Ala Ala Ala Ala Ala Ala Ser Gly Pro Gly
1               5                   10                  15

Gln Gly Gln Gly Gln Gly Gln Gly Gln Gly Gly Arg Pro Ser Asp Thr
                20                  25                  30

Tyr Gly
```

<210> SEQ ID NO 26
<211> LENGTH: 39
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(39)
<223> OTHER INFORMATION: Module R (Resilin)

<400> SEQUENCE: 26

```
Ser Ala Ala Ala Ala Ala Ala Ala Gly Pro Gly Gly Asn Gly
1               5                   10                  15

Gly Arg Pro Ser Asp Thr Tyr Gly Ala Pro Gly Gly Asn Gly Gly
                20                  25                  30

Arg Pro Ser Ser Ser Tyr Gly
            35
```

<210> SEQ ID NO 27
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(4)
<223> OTHER INFORMATION: peptide linker

<400> SEQUENCE: 27

```
Gly Gly Lys Gly
1
```

<210> SEQ ID NO 28
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(4)
<223> OTHER INFORMATION: peptide linker

<400> SEQUENCE: 28

```
Gly Lys Gly Gly
1
```

<210> SEQ ID NO 29
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module Ac

<400> SEQUENCE: 29

```
Gly Pro Tyr Gly Pro Gly Ala Ser Ala Ala Ala Ala Ala Gly Gly
1               5                   10                  15

Tyr Gly Pro Gly Cys Gly Gln Gln
            20
```

<210> SEQ ID NO 30
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module Ak

<400> SEQUENCE: 30

```
Gly Pro Tyr Gly Pro Gly Ala Ser Ala Ala Ala Ala Ala Gly Gly
1               5                   10                  15

Tyr Gly Pro Gly Lys Gly Gln Gln
            20
```

<210> SEQ ID NO 31
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Cc

<400> SEQUENCE: 31

```
Gly Ser Ser Ala Ala Ala Ala Ala Ala Ala Ser Gly Pro Gly Gly
1               5                   10                  15

Tyr Gly Pro Glu Asn Gln Gly Pro Cys Gly Pro Gly Tyr Gly Pro
            20                  25                  30

Gly Gly Pro
        35
```

<210> SEQ ID NO 32
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ck1

<400> SEQUENCE: 32

```
Gly Ser Ser Ala Ala Ala Ala Ala Ala Ala Ser Gly Pro Gly Gly
1               5                   10                  15

Tyr Gly Pro Glu Asn Gln Gly Pro Lys Gly Pro Gly Tyr Gly Pro
            20                  25                  30

Gly Gly Pro
        35
```

<210> SEQ ID NO 33
<211> LENGTH: 35
<212> TYPE: PRT
<213> ORGANISM: Artificial Sequence
<220> FEATURE:

<223> OTHER INFORMATION: synthetic
<220> FEATURE:
<221> NAME/KEY: DOMAIN
<222> LOCATION: (1)..(35)
<223> OTHER INFORMATION: Module Ck2

<400> SEQUENCE: 33

Gly Ser Ser Ala Ala Ala Ala Ala Ala Ala Ser Gly Pro Gly Gly
1               5                   10                  15

Tyr Gly Pro Lys Asn Gln Gly Pro Ser Gly Pro Gly Tyr Gly Pro
            20                  25                  30

Gly Gly Pro
        35

<210> SEQ ID NO 34
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ckc

<400> SEQUENCE: 34

Gly Ser Ser Ala Ala Ala Ala Ala Ala Ala Ser Gly Pro Gly Gly
1               5                   10                  15

Tyr Gly Pro Lys Asn Gln Gly Pro Cys Gly Pro Gly Tyr Gly Pro
            20                  25                  30

Gly Gly Pro
        35

<210> SEQ ID NO 35
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(13)
<223> OTHER INFORMATION: TAG cys1

<400> SEQUENCE: 35

Gly Cys Gly Gly Gly Gly Gly Gly Ser Gly Gly Gly Gly
1               5                   10

<210> SEQ ID NO 36
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(8)
<223> OTHER INFORMATION: TAG cys2

<400> SEQUENCE: 36

Gly Cys Gly Gly Gly Gly Gly Gly
1               5

<210> SEQ ID NO 37
<211> LENGTH: 14
<212> TYPE: PRT
<213> ORGANISM: Artificial Sequence

```
<220> FEATURE:
<223> OTHER INFORMATION: synthetic
<220> FEATURE:
<221> NAME/KEY: DOMAIN
<222> LOCATION: (1)..(14)
<223> OTHER INFORMATION: TAG cys3

<400> SEQUENCE: 37

Gly Cys Gly Gly Ser Gly Gly Gly Ser Gly Gly Gly Gly
1               5                   10

<210> SEQ ID NO 38
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(13)
<223> OTHER INFORMATION: TAG lys1

<400> SEQUENCE: 38

Gly Lys Gly Gly Gly Gly Gly Gly Ser Gly Gly Gly Gly
1               5                   10

<210> SEQ ID NO 39
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(8)
<223> OTHER INFORMATION: TAG lys2

<400> SEQUENCE: 39

Gly Lys Gly Gly Gly Gly Gly Gly
1               5

<210> SEQ ID NO 40
<211> LENGTH: 5
<212> TYPE: PRT
<213> ORGANISM: Arthropoda
<220> FEATURE:
<221> NAME/KEY: REPEAT
<222> LOCATION: (1)..(5)
<223> OTHER INFORMATION: peptide motif (resilin)

<400> SEQUENCE: 40

Gly Pro Gly Gln Gly
1               5

<210> SEQ ID NO 41
<211> LENGTH: 124
<212> TYPE: PRT
<213> ORGANISM: Artificial Sequence
<220> FEATURE:
<223> OTHER INFORMATION: based on ADF-3
<220> FEATURE:
<221> NAME/KEY: DOMAIN
<222> LOCATION: (1)..(124)
<223> OTHER INFORMATION: NR3 (ADF-3)

<400> SEQUENCE: 41

Gly Ala Ala Ser Ala Ala Val Ser Val Gly Gly Tyr Gly Pro Gln Ser
1               5                   10                  15

Ser Ser Ala Pro Val Ala Ser Ala Ala Ala Ser Arg Leu Ser Ser Pro
```

```
                    20                  25                  30

Ala Ala Ser Ser Arg Val Ser Ser Ala Val Ser Ser Leu Val Ser Ser
                35                  40                  45

Gly Pro Thr Asn Gln Ala Ala Leu Ser Asn Thr Ile Ser Ser Val Val
            50                  55                  60

Ser Gln Val Ser Ala Ser Asn Pro Gly Leu Ser Gly Cys Asp Val Leu
65                  70                  75                  80

Val Gln Ala Leu Leu Glu Val Val Ser Ala Leu Val Ser Ile Leu Gly
                85                  90                  95

Ser Ser Ser Ile Gly Gln Ile Asn Tyr Gly Ala Ser Ala Gln Tyr Thr
                100                 105                 110

Gln Met Val Gly Gln Ser Val Ala Gln Ala Leu Ala
                115                 120

<210> SEQ ID NO 42
<211> LENGTH: 109
<212> TYPE: PRT
<213> ORGANISM: Artificial Sequence
<220> FEATURE:
<223> OTHER INFORMATION: based on ADF-4
<220> FEATURE:
<221> NAME/KEY: DOMAIN
<222> LOCATION: (1)..(109)
<223> OTHER INFORMATION: NR4 (ADF-4)

<400> SEQUENCE: 42

Gly Ala Tyr Gly Pro Ser Pro Ser Ala Ser Ala Ser Val Ala Ala Ser
1               5                   10                  15

Arg Leu Ser Ser Pro Ala Ala Ser Ser Arg Val Ser Ser Ala Val Ser
                20                  25                  30

Ser Leu Val Ser Ser Gly Pro Thr Asn Gly Ala Ala Val Ser Gly Ala
                35                  40                  45

Leu Asn Ser Leu Val Ser Gln Ile Ser Ala Ser Asn Pro Gly Leu Ser
            50                  55                  60

Gly Cys Asp Ala Leu Val Gln Ala Leu Leu Glu Leu Val Ser Ala Leu
65                  70                  75                  80

Val Ala Ile Leu Ser Ser Ala Ser Ile Gly Gln Val Asn Val Ser Ser
                85                  90                  95

Val Ser Gln Ser Thr Gln Met Ile Ser Gln Ala Leu Ser
                100                 105

<210> SEQ ID NO 43
<211> LENGTH: 747
<212> TYPE: PRT
<213> ORGANISM: Araneus diadematus
<220> FEATURE:
<221> NAME/KEY: PEPTIDE
<222> LOCATION: (1)..(747)
<223> OTHER INFORMATION: MaSp I

<400> SEQUENCE: 43

Gln Gly Ala Gly Ala Ala Ala Ala Ala Gly Gly Ala Gly Gln Gly
1               5                   10                  15

Gly Tyr Gly Gly Leu Gly Gly Gln Gly Ala Gly Gln Gly Gly Tyr Gly
                20                  25                  30

Gly Leu Gly Gly Gln Gly Ala Gly Gln Gly Ala Gly Ala Ala Ala Ala
                35                  40                  45

Ala Ala Ala Gly Gly Ala Gly Gln Gly Gly Tyr Gly Gly Leu Gly Ser
            50                  55                  60
```

Gln Gly Ala Gly Arg Gly Gly Gln Gly Ala Gly Ala Ala Ala Ala
65                  70                  75                  80

Ala Gly Gly Ala Gly Gln Gly Gly Tyr Gly Gly Leu Gly Ser Gln Gly
                85                  90                  95

Ala Gly Arg Gly Gly Leu Gly Gly Gln Gly Ala Gly Ala Ala Ala Ala
                100                 105                 110

Ala Ala Ala Gly Gly Ala Gly Gln Gly Gly Tyr Gly Gly Leu Gly Asn
            115                 120                 125

Gln Gly Ala Gly Arg Gly Gly Gln Gly Ala Ala Ala Ala Ala Ala Gly
130                 135                 140

Gly Ala Gly Gln Gly Gly Tyr Gly Gly Leu Gly Ser Gln Gly Ala Gly
145                 150                 155                 160

Arg Gly Gly Leu Gly Gly Gln Gly Ala Gly Ala Ala Ala Ala Ala Ala
                165                 170                 175

Gly Gly Ala Gly Gln Gly Gly Tyr Gly Gly Leu Gly Gly Gln Gly Ala
            180                 185                 190

Gly Gln Gly Gly Tyr Gly Gly Leu Gly Ser Gln Gly Ala Gly Arg Gly
        195                 200                 205

Gly Leu Gly Gly Gln Gly Ala Gly Ala Ala Ala Ala Ala Ala Ala Gly
    210                 215                 220

Gly Ala Gly Gln Gly Gly Leu Gly Gly Gln Gly Ala Gly Gln Gly Ala
225                 230                 235                 240

Gly Ala Ser Ala Ala Ala Ala Gly Gly Ala Gly Gln Gly Gly Tyr Gly
                245                 250                 255

Gly Leu Gly Ser Gln Gly Ala Gly Arg Gly Gly Glu Gly Ala Gly Ala
            260                 265                 270

Ala Ala Ala Ala Ala Gly Gly Ala Gly Gln Gly Gly Tyr Gly Gly Leu
        275                 280                 285

Gly Gly Gln Gly Ala Gly Gln Gly Gly Tyr Gly Gly Leu Gly Ser Gln
    290                 295                 300

Gly Ala Gly Arg Gly Gly Leu Gly Gly Gln Gly Ala Gly Ala Ala Ala
305                 310                 315                 320

Ala Gly Gly Ala Gly Gln Gly Gly Leu Gly Gly Gln Gly Ala Gly Gln
                325                 330                 335

Gly Ala Gly Ala Ala Ala Ala Ala Gly Gly Ala Gly Gln Gly Gly
            340                 345                 350

Tyr Gly Gly Leu Gly Ser Gln Gly Ala Gly Arg Gly Gly Leu Gly Gly
        355                 360                 365

Gln Gly Ala Gly Ala Val Ala Ala Ala Ala Gly Gly Ala Gly Gln
    370                 375                 380

Gly Gly Tyr Gly Gly Leu Gly Ser Gln Gly Ala Gly Arg Gly Gly Gln
385                 390                 395                 400

Gly Ala Gly Ala Ala Ala Ala Ala Gly Gly Ala Gly Gln Arg Gly
                405                 410                 415

Tyr Gly Gly Leu Gly Asn Gln Gly Ala Gly Arg Gly Gly Leu Gly Gly
        420                 425                 430

Gln Gly Ala Gly Ala Ala Ala Ala Ala Ala Gly Gly Ala Gly Gln
    435                 440                 445

Gly Gly Tyr Gly Gly Leu Gly Asn Gln Gly Ala Gly Arg Gly Gly Gln
        450                 455                 460

Gly Ala Ala Ala Ala Ala Gly Gly Ala Gly Gln Gly Gly Tyr Gly Gly
465                 470                 475                 480

Leu Gly Ser Gln Gly Ala Gly Arg Gly Gly Gln Gly Ala Gly Ala Ala

```
            485                 490                 495
Ala Ala Ala Ala Val Gly Ala Gly Gln Glu Gly Ile Arg Gly Gln Gly
            500                 505                 510

Ala Gly Gln Gly Gly Tyr Gly Gly Leu Gly Ser Gln Gly Ser Gly Arg
            515                 520                 525

Gly Gly Leu Gly Gly Gln Gly Ala Gly Ala Ala Ala Ala Ala Ala Gly
            530                 535                 540

Gly Ala Gly Gln Gly Gly Leu Gly Gly Gln Gly Ala Gly Gln Gly Ala
545                 550                 555                 560

Gly Ala Ala Ala Ala Ala Gly Gly Val Arg Gln Gly Gly Tyr Gly
            565                 570                 575

Gly Leu Gly Ser Gln Gly Ala Gly Arg Gly Gly Gln Gly Ala Gly Ala
            580                 585                 590

Ala Ala Ala Ala Ala Gly Gly Ala Gly Gln Gly Gly Tyr Gly Gly Leu
            595                 600                 605

Gly Gly Gln Gly Val Gly Arg Gly Gly Leu Gly Gly Gln Gly Ala Gly
            610                 615                 620

Ala Ala Ala Ala Gly Gly Ala Gly Gln Gly Gly Tyr Gly Gly Val Gly
625                 630                 635                 640

Ser Gly Ala Ser Ala Ala Ser Ala Ala Ala Ser Arg Leu Ser Ser Pro
            645                 650                 655

Gln Ala Ser Ser Arg Val Ser Ser Ala Val Ser Asn Leu Val Ala Ser
            660                 665                 670

Gly Pro Thr Asn Ser Ala Ala Leu Ser Ser Thr Ile Ser Asn Val Val
            675                 680                 685

Ser Gln Ile Gly Ala Ser Asn Pro Gly Leu Ser Gly Cys Asp Val Leu
            690                 695                 700

Ile Gln Ala Leu Leu Glu Val Val Ser Ala Leu Ile Gln Ile Leu Gly
705                 710                 715                 720

Ser Ser Ser Ile Gly Gln Val Asn Tyr Gly Ser Ala Gly Gln Ala Thr
            725                 730                 735

Gln Ile Val Gly Gln Ser Val Tyr Gln Ala Leu
            740                 745

<210> SEQ ID NO 44
<211> LENGTH: 627
<212> TYPE: PRT
<213> ORGANISM: Araneus diadematus
<220> FEATURE:
<221> NAME/KEY: PEPTIDE
<222> LOCATION: (1)..(627)
<223> OTHER INFORMATION: MaSp II

<400> SEQUENCE: 44

Pro Gly Gly Tyr Gly Pro Gly Gln Gln Gly Pro Gly Gly Tyr Gly Pro
1               5                   10                  15

Gly Gln Gln Gly Pro Ser Gly Pro Gly Ser Ala Ala Ala Ala Ala Ala
            20                  25                  30

Ala Ala Ala Ala Gly Pro Gly Gly Tyr Gly Pro Gly Gln Gln Gly Pro
            35                  40                  45

Gly Gly Tyr Gly Pro Gly Gln Gln Gly Pro Gly Arg Tyr Gly Pro Gly
            50                  55                  60

Gln Gln Gly Pro Ser Gly Pro Gly Ser Ala Ala Ala Ala Ala Gly
65                  70                  75                  80

Ser Gly Gln Gln Gly Pro Gly Gly Tyr Gly Pro Arg Gln Gln Gly Pro
            85                  90                  95
```

```
Gly Gly Tyr Gly Gln Gly Gln Gln Gly Pro Ser Gly Pro Gly Ser Ala
            100                 105                 110

Ala Ala Ala Ser Ala Ala Ala Ser Ala Glu Ser Gly Gln Gln Gly Pro
            115                 120                 125

Gly Gly Tyr Gly Pro Gly Gln Gln Gly Pro Gly Gly Tyr Gly Pro Gly
            130                 135                 140

Gln Gln Gly Pro Gly Gly Tyr Gly Pro Gly Gln Gln Gly Pro Ser Gly
145                 150                 155                 160

Pro Gly Ser Ala Ala Ala Ala Ala Ala Ala Ser Gly Pro Gly Gln
            165                 170                 175

Gln Gly Pro Gly Gly Tyr Gly Pro Gly Gln Gln Gly Pro Gly Gly Tyr
            180                 185                 190

Gly Pro Gly Gln Gln Gly Pro Ser Gly Pro Gly Ser Ala Ala Ala Ala
            195                 200                 205

Ala Ala Ala Ser Gly Pro Gly Gln Gln Gly Pro Gly Gly Tyr Gly
            210                 215                 220

Pro Gly Gln Gln Gly Pro Gly Gly Tyr Gly Pro Gly Gln Gln Gly Leu
225                 230                 235                 240

Ser Gly Pro Gly Ser Ala Ala Ala Ala Ala Ala Gly Pro Gly Gln
            245                 250                 255

Gln Gly Pro Gly Gly Tyr Gly Pro Gly Gln Gln Gly Pro Ser Gly Pro
            260                 265                 270

Gly Ser Ala Ala Ala Ala Ala Ala Ala Gly Pro Gly Gly Tyr
            275                 280                 285

Gly Pro Gly Gln Gln Gly Pro Gly Gly Tyr Gly Pro Gly Gln Gln Gly
            290                 295                 300

Pro Ser Gly Ala Gly Ser Ala Ala Ala Ala Ala Ala Gly Pro Gly
305                 310                 315                 320

Gln Gln Gly Leu Gly Gly Tyr Gly Pro Gly Gln Gln Gly Pro Gly Gly
            325                 330                 335

Tyr Gly Pro Gly Gln Gln Gly Pro Gly Gly Tyr Gly Pro Gly Ser Ala
            340                 345                 350

Ser Ala Ala Ala Ala Ala Ala Gly Pro Gly Gln Gln Gly Pro Gly Gly
            355                 360                 365

Tyr Gly Pro Gly Gln Gln Gly Pro Ser Gly Pro Gly Ser Ala Ser Ala
            370                 375                 380

Ala Ala Ala Ala Ala Ala Gly Pro Gly Gly Tyr Gly Pro Gly Gln
385                 390                 395                 400

Gln Gly Pro Gly Gly Tyr Ala Pro Gly Gln Gln Gly Pro Ser Gly Pro
            405                 410                 415

Gly Ser Ala Ser Ala Ala Ala Ala Ala Ala Gly Pro Gly Gly
            420                 425                 430

Tyr Gly Pro Gly Gln Gln Gly Pro Gly Gly Tyr Ala Pro Gly Gln Gln
            435                 440                 445

Gly Pro Ser Gly Pro Gly Ser Ala Ala Ala Ala Ala Ala Ala Ala
            450                 455                 460

Gly Pro Gly Gly Tyr Gly Pro Ala Gln Gln Gly Pro Ser Gly Pro Gly
465                 470                 475                 480

Ile Ala Ala Ser Ala Ala Ser Ala Gly Pro Gly Gly Tyr Gly Pro Ala
            485                 490                 495

Gln Gln Gly Pro Ala Gly Tyr Gly Pro Gly Ser Ala Val Ala Ala Ser
            500                 505                 510
```

```
Ala Gly Ala Gly Ser Ala Gly Tyr Gly Pro Gly Ser Gln Ala Ser Ala
        515                 520                 525

Ala Ala Ser Arg Leu Ala Ser Pro Asp Ser Gly Ala Arg Val Ala Ser
    530                 535                 540

Ala Val Ser Asn Leu Val Ser Ser Gly Pro Thr Ser Ser Ala Ala Leu
545                 550                 555                 560

Ser Ser Val Ile Ser Asn Ala Val Ser Gln Ile Gly Ala Ser Asn Pro
                565                 570                 575

Gly Leu Ser Gly Cys Asp Val Leu Ile Gln Ala Leu Leu Glu Ile Val
            580                 585                 590

Ser Ala Cys Val Thr Ile Leu Ser Ser Ser Ser Ile Gly Gln Val Asn
        595                 600                 605

Tyr Gly Ala Ala Ser Gln Phe Ala Gln Val Val Gly Gln Ser Val Leu
    610                 615                 620

Ser Ala Phe
625

<210> SEQ ID NO 45
<211> LENGTH: 136
<212> TYPE: PRT
<213> ORGANISM: artificial
<220> FEATURE:
<223> OTHER INFORMATION: synthetic
<220> FEATURE:
<221> NAME/KEY: domain
<222> LOCATION: (1)..(136)
<223> OTHER INFORMATION: derived from Latrodectus hesperus

<400> SEQUENCE: 45

Met Gly Gln Ala Asn Thr Pro Trp Ser Ser Lys Ala Asn Ala Asp Ala
1               5                   10                  15

Phe Ile Asn Ser Phe Ile Ser Ala Ala Ser Asn Thr Gly Ser Phe Ser
            20                  25                  30

Gln Asp Gln Met Glu Asp Met Ser Leu Ile Gly Asn Thr Leu Met Ala
        35                  40                  45

Ala Met Asp Asn Met Gly Gly Arg Ile Thr Pro Ser Lys Leu Gln Ala
    50                  55                  60

Leu Asp Met Ala Phe Ala Ser Ser Val Ala Glu Ile Ala Ala Ser Glu
65                  70                  75                  80

Gly Gly Asp Leu Gly Val Thr Thr Asn Ala Ile Ala Asp Ala Leu Thr
                85                  90                  95

Ser Ala Phe Tyr Gln Thr Thr Gly Val Val Asn Ser Arg Phe Ile Ser
            100                 105                 110

Glu Ile Arg Ser Leu Ile Gly Met Phe Ala Gln Ala Ser Ala Asn Asp
        115                 120                 125

Val Tyr Ala Ser Ala Gly Ser Gly
    130                 135

<210> SEQ ID NO 46
<211> LENGTH: 137
<212> TYPE: PRT
<213> ORGANISM: artificial
<220> FEATURE:
<223> OTHER INFORMATION: synthetic
<220> FEATURE:
<221> NAME/KEY: domain
<222> LOCATION: (1)..(137)
<223> OTHER INFORMATION: derived from Latrodectus hesperus

<400> SEQUENCE: 46
```

-continued

```
Met Gly Gln Ala Asn Thr Pro Trp Ser Ser Lys Glu Asn Ala Asp Ala
1               5                   10                  15

Phe Ile Gly Ala Phe Met Asn Ala Ala Ser Gln Ser Gly Ala Phe Ser
                20                  25                  30

Ser Asp Gln Ile Asp Asp Met Ser Val Ile Ser Asn Thr Leu Met Ala
            35                  40                  45

Ala Met Asp Asn Met Gly Gly Arg Ile Thr Gln Ser Lys Leu Gln Ala
    50                  55                  60

Leu Asp Met Ala Phe Ala Ser Ser Val Ala Glu Ile Ala Val Ala Asp
65                  70                  75                  80

Gly Gln Asn Val Gly Ala Ala Thr Asn Ala Ile Ser Asp Ala Leu Arg
                85                  90                  95

Ser Ala Phe Tyr Gln Thr Thr Gly Val Val Asn Asn Gln Phe Ile Thr
            100                 105                 110

Gly Ile Ser Ser Leu Ile Gly Met Phe Ala Gln Val Ser Gly Asn Glu
            115                 120                 125

Val Ser Tyr Ser Ser Ala Gly Ser Gly
    130                 135
```